(12) United States Patent
Salituro et al.

(10) Patent No.: US 6,509,363 B2
(45) Date of Patent: Jan. 21, 2003

(54) HETEROCYCLIC INHIBITORS OF P38

(75) Inventors: Francesco Salituro, Marlborough; Guy Bemis, Arlington; John Cochran, North Andover, all of MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 41 days.

(21) Appl. No.: 09/809,854

(22) Filed: Mar. 16, 2001

(65) Prior Publication Data

US 2002/0016471 A1 Feb. 7, 2002

Related U.S. Application Data

(63) Continuation of application No. PCT/US99/21337, filed on Sep. 16, 1999.
(60) Provisional application No. 60/100,970, filed on Sep. 18, 1998.

(51) Int. Cl.$^7$ .................. A61K 31/421; A61K 31/426; A61K 31/4168; C07D 277/48; C07D 263/48
(52) U.S. Cl. ................. 514/371; 514/377; 514/398; 548/196; 548/234; 548/333.1
(58) Field of Search ............................... 548/333.1, 196, 548/234; 514/371, 377, 398

(56) References Cited

FOREIGN PATENT DOCUMENTS

| DE | 896809 C | 9/1952 |
| DE | 897406 | * 11/1953 |
| EP | 0424021 A1 | 4/1991 |
| WO | WO 98/27098 A1 | 6/1998 |

OTHER PUBLICATIONS

Erne, Helv. Chim. Acta, 36(1953), pp. 138–141.*
Hanson, G.J. "Inhibitors of p38 Kinase" *Expert Opinion On Therapeutic Patents*, 7(7): 729–733 (1997).

* cited by examiner

*Primary Examiner*—Laura L. Stockton
(74) *Attorney, Agent, or Firm*—Fish & Neave; James F. Haley, Jr.; Kristin M. Joslyn

(57) ABSTRACT

The present invention relates to inhibitors of p38, a mammalian protein kinase involved cell proliferation, cell death and response to extracellular stimuli. The invention also relates to methods for producing these inhibitors. The invention also provides pharmaceutical compositions comprising the inhibitors of the invention and methods of utilizing those compositions in the treatment and prevention of various disorders.

32 Claims, No Drawings

HETEROCYCLIC INHIBITORS OF P38

This application is a continuation of International application Ser. No. PCT/US99/21337, filed Sep. 16, 1999, which claims the benefit of U.S. Provisional Application Ser. No. 60/100,972, filed Sep. 18, 1998.

TECHNICAL FIELD OF INVENTION

The present invention relates to inhibitors of p38, a mammalian protein kinase is involved in cell proliferation, cell death and response to extracellular stimuli. The invention also relates to methods for producing these inhibitors. The invention also provides pharmaceutical compositions comprising the inhibitors of the invention and methods of utilizing those compositions in the treatment and prevention of various disorders.

BACKGROUND OF THE INVENTION

Protein kinases are involved in various cellular responses to extracellular signals. Recently, a family of mitogen-activated protein kinases (MAPK) has been discovered. Members of this family are Ser/Thr kinases that activate their substrates by phosphorylation [B. Stein et al., *Ann. Rep. Med. Chem.*, 31, pp. 289–98 (1996)]. MAPKs are themselves activated by a variety of signals including growth factors, cytokines, UV radiation, and stress-inducing agents.

One particularly interesting MAPK is p38. p38, also known as cytokine suppressive anti-inflammatory drug binding protein (CSBP) and RK, is isolated from murine pre-B cells that are transfected with the lipopolysaccharide (LPS) receptor, CD14, and induced with LPS. p38 has since been isolated and sequenced, as has the cDNA encoding it in humans and mouse. Activation of p38 has been observed in cells stimulated by stress, such as treatment of lipopolysaccharides (LPS), UV, anisomycin, or osmotic shock, and by treatment with cytokines, such as IL-1 and TNF.

Inhibition of p38 kinase leads to a blockade in the production of both IL-1 and TNF. IL-1 and TNF stimulate the production of other proinflammatory cytokines such as IL-6 and IL-8 and have been implicated in acute and chronic inflammatory diseases and in post-menopausal osteoporosis [R. B. Kimble et al., *Endocrinol.*, 136, pp. 3054–61 (1995)].

Based upon this finding it is believed that p38, along with other MAPKs, have a role in mediating cellular response to inflammatory stimuli, such as leukocyte accumulation, macrophage/monocyte activation, tissue resorption, fever, acute phase responses and neutrophilia. In addition, MAPKs, such as p38, have been implicated in cancer, thrombin-induced platelet aggregation, immunodeficiency disorders, autoimmune diseases, cell death, allergies, osteoporosis and neurodegenerative disorders. Inhibitors of p38 have been implicated in the area of pain management through inhibition of prostaglandin endoperoxide synthase-2 induction. Other diseases associated with IL-1, IL-6, IL-8 or TNF overproduction are set forth in WO 96/21654.

Others have already begun trying to develop drugs that specifically inhibit MAPKs. For example, PCT publication WO 95/31451 describes pyrazole compounds that inhibit MAPKs, and, in particular, p38. However, the efficacy of these inhibitors in vivo is still being investigated.

Accordingly, there is still a great need to develop other potent, p38-specific inhibitors that are useful in treating various conditions associated with p38 activation.

SUMMARY OF THE INVENTION

The present invention addresses this problem by providing compounds that demonstrate strong and specific inhibition of p38.

These compounds have the general formulae:

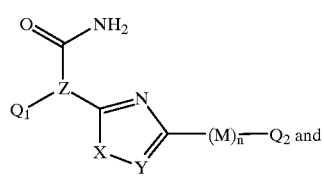

I

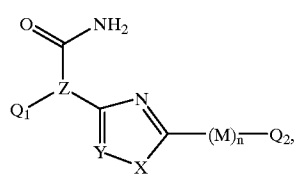

II or pharmaceutically acceptable salts thereof, wherein each of $Q_1$ and $Q_2$ are independently selected from 5–6 membered aromatic carbocyclic or heterocyclic ring systems, or 8–10 membered bicyclic ring systems comprising aromatic carbocyclic rings, aromatic heterocyclic rings or a combination of an aromatic carbocyclic ring and an aromatic heterocyclic ring. Alternatively, $Q_1$ is selected from a 5–6 membered aromatic carbocyclic or heterocyclic ring system, or an 8–10 membered bicyclic ring system comprising aromatic carbocyclic rings, aromatic heterocyclic rings or a combination of an aromatic carbocyclic ring and an aromatic heterocyclic ring, and $Q_2$ is selected from H, $CO_2R'$, CON$(R')_2$, or a $(C_1-C_4)$ branched or straight-chain alkyl optionally containing 1–3 substituents independently selected from A, T—C (O) R', $OPO_3H_2$, NR'$_2$, N(R')$_2$, OR', $CO_2R'$, CON(R')$_2$, or $SO_2N(R^2)_2$.

The rings that make up $Q_1$ are optionally substituted with 1 to 4 substituents, each of which is independently selected from halo; $C_1-C_4$ alkyl optionally containing 1–3 substituents independently selected from A, T—C (O) R', $OPO_3H_2$, NR'$_2$, NR'$_2$, OR', $CO_2R'$ or CONR'$_2$; O—(C$_1$–C$_4$)-alkyl optionally containing 1–3 substituents independently selected from A, T—C (O) R', $OPO_3H_2$, NR'$_2$, NR'$_2$, OR', $CO_2R'$ or CONR'$_2$; NR'$_2$; OCF$_3$; CF$_3$; NO$_2$; CO$_2R'$; CONR'; SR'; S (O$_2$) N (R')$_2$; SCF$_3$; CN; N (R') C (O) R$^4$; N (R') C (O) OR$^4$; N (R') C (O) C (O) R$^4$; N (R') S (O$_2$) R$^4$; N (R') R$^4$; N (R$^4$)$_2$; OR$^4$; OC(O)R$^4$; OP(O)$_3$H$_2$; or N=C—N(R')$_2$.

When $Q_2$ is a ring system, the rings that make up $Q_2$ are optionally substituted with up to 4 substituents, each of which is independently selected from halo; $C_1-C_4$ straight or branched alkyl optionally containing 1–3 substitutents independently selected from A, T—C (O) R', $OPO_3H_2$, NR'$_2$, OR', CO$_2R'$, S (O$_2$) N (R')$_2$, N=C—N (R')$_2$, R$^3$, or CONR'$_2$; O—(C$_1$–C$_3$)-alkyl; O—(C$_1$–C$_4$)-alkyl optionally containing 1–3 substituents independently selected from A, T—C (O) R', OPO$_3$H$_2$, NR'$_2$, NR'$_2$, OR', CO$_2R'$, S (O$_2$)N(R')$_2$, N=C—N (R')$_2$, R$^3$, or CONR'$_2$; NR'$_2$; OCF$_3$; CF$_3$; NO$_2$; CO$_2R'$; CONR'; R$^3$; OR$^3$; NR$^3$; SR$^3$; C (O) R$^3$; C (O) N (R') R$^3$; C (O) OR$^3$; SR'; S (O$_2$) N (R')$_2$; SCF$_3$; N=C—N(R')$_2$; or CN.

A is selected from the groups:

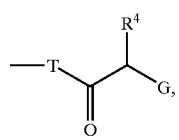 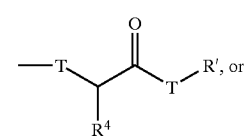

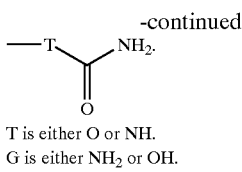

T is either O or NH.
G is either NH$_2$ or OH.

R' is selected from hydrogen, (C$_1$–C$_3$)-alkyl; (C$_2$–C$_3$)-alkenyl or alkynyl; phenyl or phenyl substituted with 1 to 3 substituents independently selected from halo, methoxy, cyano, nitro, amino, hydroxy, methyl or ethyl.

R$^3$ is selected from 5–6 membered aromatic carbocyclic or heterocyclic ring systems.

R$^4$ is (C$_1$–C$_4$)-alkyl optionally substituted with N (R')$_2$, OR$^{40}$, CO$_2$R', CON (R')$_2$, or SO$_2$N(R$^2$)$_2$; a 5–6 membered carbocyclic or heterocyclic ring system optionally substituted with a (C$_1$–C$_4$) branched or straight-chain alkyl group, N (R')$_2$, OR', CO$_2$R', CON (R')$_2$, or SO$_2$N(R$^2$ )$_2$; or a (C$_1$–C$_4$)-alkyl optionally substituted with the 5–6 membered carbocyclic or heterocyclic ring system optionally substituted as described immediately above.

R$^2$ is selected from hydrogen, (C$_1$–C$_3$)-alkyl, or (C$_1$–C$_3$)-alkenyl; each optionally substituted with —N (R')$_2$, —OR', SR', —C (O) —N (R')$_2$, —S (O$_2$) —N(R')$_2$, —C (O) —OR', or R$^3$.

X is selected from O, S, NR or C(R)$_2$.
Y is CR or N.
Z is CH or N.
M is C=O, CHOH, or CH$_2$.
n is 0 or 1.

Each R is independently selected from hydrogen, —R$^2$, —N (R$^2$)$_2$, —OR$^2$, SR$^2$, —C (O$_2$) —N (R$^2$)$_2$, or —C (O) —OR$^2$, wherein two adjacent R are optionally bound to one another and, together with each Y to which they are respectively bound, form a 4–8 membered carbocyclic or heterocyclic ring.

In another embodiment, the invention provides pharmaceutical compositions comprising the p38 inhibitors of this invention. These compositions may be utilized in methods for treating or preventing a variety of disorders, such as cancer, inflammatory diseases, autoimmune diseases, destructive bone disorders, proliferative disorders, infectious diseases, viral diseases and neurodegenerative and neurological diseases. These compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. Each of these above-described methods is also part of the present invention.

In another embodiment, compounds of the instant invention may act as Jnk3 inhibitors. Jnk3 is a MAP kinase involved in nervous system development, maintenance and repair, and may be important for stress-induced neuronal apoptosis in the central nervous system (Yang et al., Nature 389: 865–870, 1997). These compounds may be used to formuate pharmaceutical compositions that can be used for methods of treating Jnk3-mediated neurological diseases.

DETAILED DESCRIPTION OF THE INVENTION

In order that the invention herein described may be more fully understood, the following detailed description is set forth. In the description, the following terms are employed:

The term "heterocyclyl" or "heterocycle" refers to a stable 5–6 membered monocyclic heterocyclic ring or 8–10 membered bicyclic heterocyclic ring which is either saturated or unsaturated, and which may be optionally benzofused if monocyclic. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heterocyclyl radical may be attached at any endocyclic carbon or heteroatom that results in the creation of a stable structure. Examples of such groups include imidazolyl, imidazolinoyl, imidazolidinyl, quinolyl, isoqinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, carbolinyl, tetrazolyl, thiazolidinyl, benzofuranoyl, thiamorpholinyl sulfone, oxazolyl, benzoxazolyl, oxopiperidinyl, oxopyrrolidinyl, oxoazepinyl, azepinyl, isoxozolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetrahydrofurodihydrofuranyl, tetrahydropyranodihydrofuranyl, dihydropyranyl, tetradyrofurofuranyl and tetrahydropyranofuranyl.

The term "carbocyclyl" or "carbocycle" refers to a stable 5–6 membered monocyclic carbocyclic ring or 8–10 membered bicyclic carbocyclic ring which is either saturated or unsaturated, and which may be optionally benzofused if monocyclic.

The term "pharmaceutically acceptable salts" refers to compounds according to the invention used in the form of salts derived from inorganic or organic acids and bases.

Included among acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectianate, persulfate, phenylproprionate, picrate, pivalate, propionate, succinate, tartrate, thiocyanate, tosylate and undecanoate.

Salts derived from appropriate bases include alkali metal (e.g. sodium), alkaline earth metal (e.g., magnesium), ammonium and NW$_4^+$ (wherein W is C$_{1-4}$ alkyl). Physiologically acceptable salts of a hydrogen atom or an amino group include salts or organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as Na$^+$, NH$_4^+$, and NW$_4^+$ (wherein W is a C$_{1-4}$ alkyl group).

Pharmaceutically acceptable salts include salts of organic carboxylic acids such as ascorbic, acetic, citric, lactic, tartaric, malic, maleic, isothionic, lactobionic, p-aminobenzoic and succinic acids; organic sulphonic acids such as methanesulphonic, ethanesulphonic, benzenesulphonic and p-toluenesulphonic acids and inorganic acids such as hydrochloric, sulphuric, phosphoric, sulphamic and pyrophosphoric acids.

For therapeutic use, salts of the compounds according to the invention will be pharmaceutically acceptable. However, salts of acids and bases that are not pharmaceutically acceptable may also find use, for example, in the preparation or purification of a pharmaceutically acceptable compound.

Preferred salts include salts formed from hydrochloric, sulfuric, acetic, succinic, citric and ascorbic acids.

The term "chemically feasible" refers to a connectivity of atoms such that the chemical valency of each atom is satisfied. For example, an oxygen atom with two bonds and a carbon atom with four bonds are chemically feasible.

The term "tautomerization" refers to the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69–74 (1992). The term "tautomer" refers to the compounds produced by the proton shift.

The present invention provides inhibitors of p38 having the general formulae:

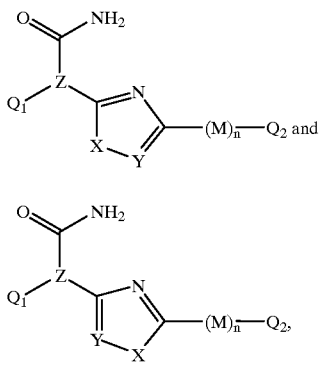

or pharmaceutically acceptable salts thereof, wherein each of $Q_1$ and $Q_2$ are independently selected from 5–6 membered aromatic carbocyclic or heterocyclic ring systems, or 8–10 membered bicyclic ring systems comprising aromatic carbocyclic rings, aromatic heterocyclic rings or a combination of an aromatic carbocyclic ring and an aromatic heterocyclic ring. Alternatively, $Q_1$ is selected from a 5–6 membered aromatic carbocyclic or heterocyclic ring system, or an 8–10 membered hicyclic ring system comprising aromatic carbocyclic rings, aromatic heterocyclic rings or a combination of an aromatic carbocyclic ring and an aromatic heterocyclic ring, and $Q_2$ is selected from H, $CO_2R'$, CON (R')$_2$, or a ($C_1$–$C_4$) branched or straight-chain alkyl optionally containing 1–3 substituents independently selected from A, T—C (O) R', $OPO_3H_2$, $NR'_2$, N (R')$_2$, OR', $CO_2R'$, CON (R')$_2$, or $SO_2N$ ($R^2$)$_2$.

The rings that make up $Q_1$ are optionally substituted with 1 to 4 substituents, each of which is independently selected from halo; $C_1$–$C_4$ alkyl optionally containing 1–3 substituents independently selected from A, T—C (O) R', $OPO_3H_2$, $NR'_2$, $NR'_2$, OR', $CO_2R'$ or $CONR'_2$; O—($C_1$–$C_4$)-alkyl optionally containing 1–3 substituents independently selected from A, T—C (O) R', $OPO_3H_2$, $NR'_2$, OR', $CO_2R'$ or $CONR'_2$; $NR'_2$; $OCF_3$; $CF_3$; $NO_2$; $CO_2R'$; CONR'; SR'; S ($O_2$) N (R')$_2$; $SCF_3$; CN; N (R') C (O) $R^4$; N (R') C (O) $OR^4$; N (R') C (O) C (O) $R^4$; N (R') S ($O_2$) $R^4$; N (R') $R^4$; N ($R^4$)$_2$; $OR^4$ OC (C) $R^4$; OP (O) $_3H_2$; or N=C—N (R')$_2$.

When $Q_2$ is a ring system, the rings that make up $Q_2$ are optionally substituted with up to 4 substituents, each of which is independently selected from halo; $C_1$–$C_4$ straight or branched alkyl optionally containing 1–3 substituents independently selected from A, T—C (O) R', $OPO_3H_2$, $NR'_2$, OR', $CO_2R'$, S ($O_2$) N (R')$_2$, N=C—N(R')$_2$, $R^3$, or $CONR'_2$; O—($C_1$–$C_3$)-alkyl; O—($C_1$–$C_4$)-alkyl optionally containing 1–3 substituents independently selected from A, T—C (O) R—, $OPO_3H_2$, $NR'_2$, $NR'_2$, OR', $CO_2R'$, S ($O_2$) N (R')$_2$, N=C—N (R')$_2$, $R^3$, or $CONR'_2$; $NR'_2$; $OCF_3$; $CF_3$; $NO_2$; $CO_2R'$; CONR'; $R^3$; $OR^3$; $NR^3$; $SR^3$; $C(O)R^3$; $C(O)N(R')R^3$; $C(O)OR^3$; SR'; S ($O_2$) N (R')$_2$; $SCF_3$; N=C—N (R')$_2$; or CN.

A is selected from the groups:

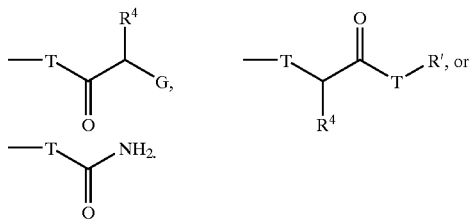

T is either 0 or NH.
G is either $NH_2$ or OH.
R' is selected from hydrogen, ($C_1$–$C_3$)-alkyl; ($C_2$–$C_3$)-alkenyl or alkynyl; phenyl or phenyl substituted with 1 to 3 substituents independently selected from halo, methoxy, cyano, nitro, amino, hydroxy, methyl or ethyl.
$R^3$ is selected from 5–6 membered aromatic carbocyclic or heterocyclic ring systems.
$R^4$ is ($C_1$–$C_4$)-alkyl optionally substituted with N (R')$_2$, OR', $CO_2R'$, CON(R')$_2$, or $SO_2N$ ($R^2$)$_2$; a 5–6 membered carbocyclic or heterocyclic ring system optionally substituted with a ($C_1$–$C_4$) branched or straight-chain alkyl group, N (R')$_2$, OR', $CO_2R'$, CON (R')$_2$, or $SO_2N$ ($R^2$)$_2$; or a ($C_1$–$C_4$)-alkyl optionally substituted with the 5–6 membered carbocyclic or heterocyclic ring system optionally substituted as described immediately above.
$R^2$ is selected from hydrogen, ($C_1$–$C_3$)-alkyl, or ($C_1$–$C_3$)-alkenyl; each optionally substituted with —N(R')$_2$ —OR', SR', —C (O) —N (R')$_2$, —S ($O_2$) —N (R')$_2$, —C (O) —OR', or $R^3$.
X is selected from 0, S, NR or C (R)$_2$.
Y is CR or N.
Z is CH or N.
M is C=O, CHOH, or $CH_2$.
n is 0 or 1.
Each R is independently selected from hydrogen, —$R^2$, —N ($R^2$)$_2$, —$OR^2$, $SR^2$, —C (O) —N ($R^2$)$_2$, —S ($O_2$) —N($R^2$)$_2$, or —C (O) —$OR^2$, wherein two adjacent R are optionally bound to one another and, together with each Y to which they are respectively bound, form a 4–8 membered carbocyclic or heterocyclic ring.

It will be apparent to one of skill in the art that the compounds of the present invention may exist as tautomers. Such tautomers may be transient or isolatable as a stable product. These tautomers are envisioned within the scope of the invention. These compounds are also p38 inhibitors and fall within the scope of the present invention.

According to another preferred embodiment, $Q_1$ is selected from phenyl or pyridyl containing 1 to 3 substituents, wherein at least one of said substituents is in the ortho position and said substituents are independently selected from chloro, fluoro, bromo, —$CH_3$, —$OCH_3$, —OH, —$CF_3$, —$OCF_3$, —O ($CH_2$)$_2CH_3$, $NH_2$, 3,4-methylenedioxy, —N ($CH_3$)$_2$, —NH—S ($O$)$_2$-phenyl, —NH—C (O) O—$CH_{2-4}$-pyridine, —NH—C (O) $CH_2$- morpholine, —NH—C (O) CH$_2$—N (CH$_3$)$_2$, —NH—C (O) CH$_2$-piperazine, —NH—C (O) CH$_2$-pyrrolidine, —NH—C (O) C (O)-morpholine, —NH—C (O) C (O)-piperazine, —NH—C (O) C (O)-pyrrolidine, —O—C (O )CH$_2$—N (CH$_3$)$_2$, or —O—(CH$_2$)$_2$—N (CH$_3$)$_2$.
Even more preferred are phenyl or pyridyl containing at least 2 of the above-indicated substituents both being in the ortho position.
Some specific examples of preferred Q$_1$ are:
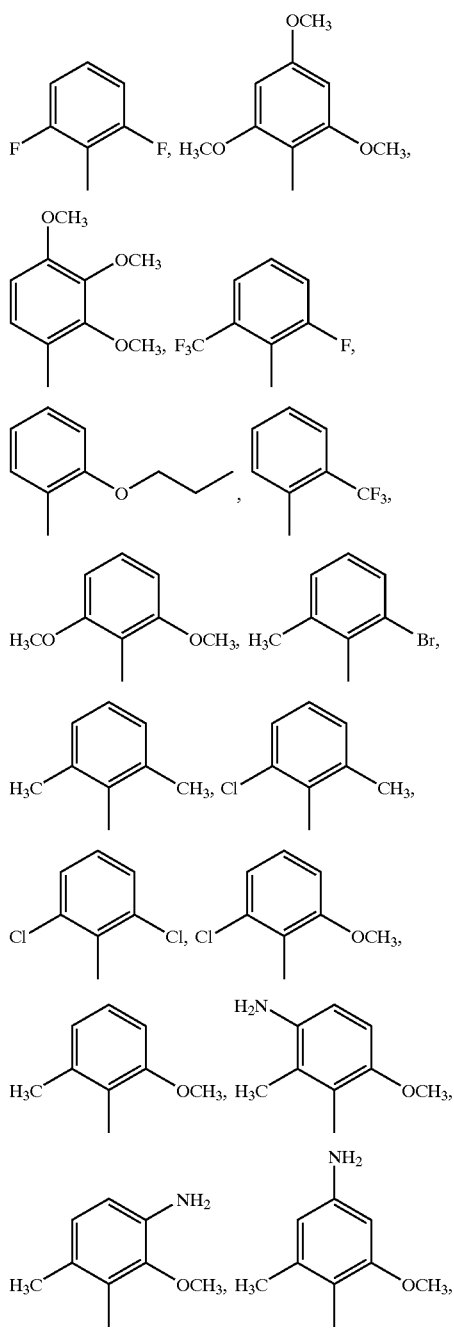
-continued
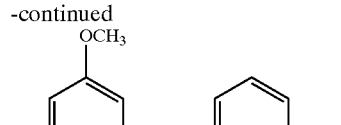

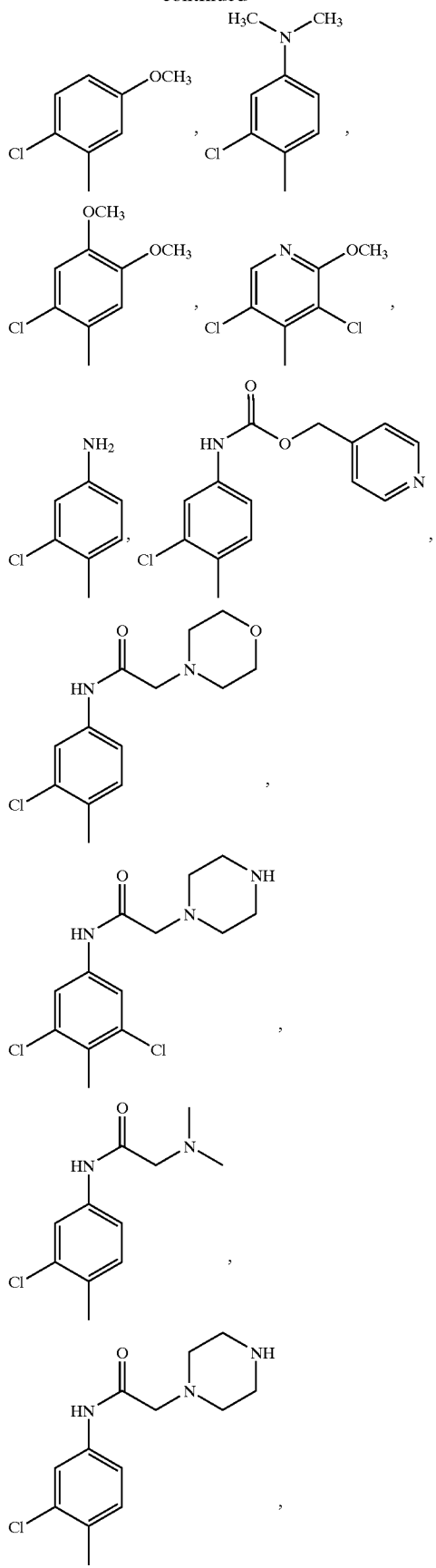
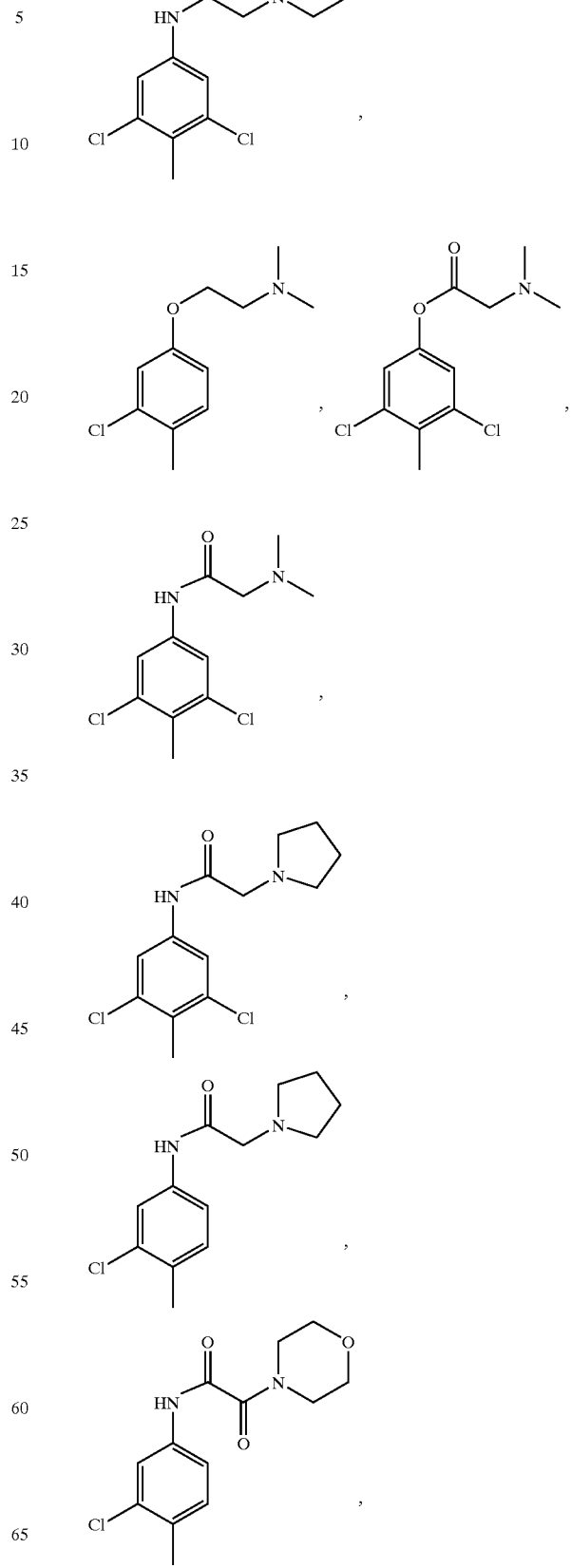

-continued

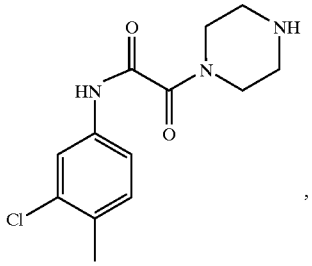

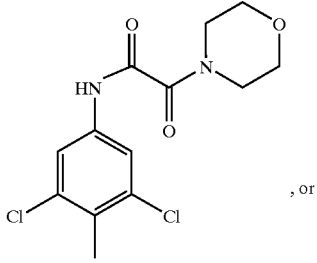, or

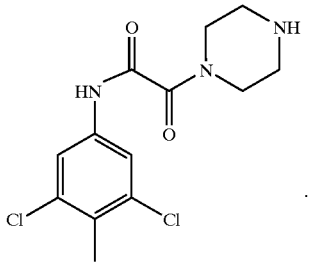.

Most preferably, $Q_1$ is selected from 2-fluoro-6-trifluoromethylphenyl; 2,6-difluorophenyl; 2,6-dichlorophenyl; 2-chloro-4-hydroxyphenyl; 2-chloro-4-aminophenyl; 2,6-dichloro-4-aminophenyl; 2,6-dichloro-3-amninophenyl; 2,6-dimethyl-4-hydroxyphenyl; 2-methoxy-3,5-dichloro-4-pyridyl; 2-chloro-4,5 methylenedioxy phenyl; or 2-chloro-4-(N-2-morpholino-acetamido)phenyl.

According to a preferred embodiment, $Q_2$ is phenyl or pyridyl containing 0 to 3 substituents, wherein each substituent is independently selected from chloro, fluoro, bromo, methyl, ethyl, isopropyl, —OCH$_3$, —OH, —NH$_2$, —CF$_3$, —OCF$_3$, —SCH$_3$, —OCH$_3$, —C(O)OH, —C(O)OCH$_3$, —CH$_2$NH$_2$, —N(CH$_3$)$_2$, —CH$_2$-pyrrolidine and —CH$_2$OH.

Some specific examples of preferred $Q_2$ are:

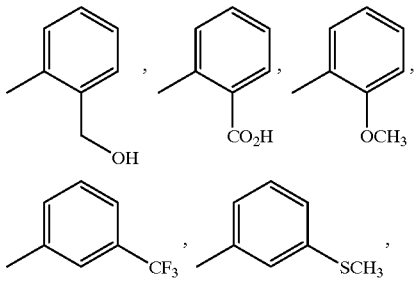

-continued

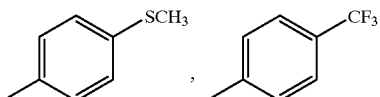

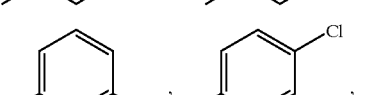

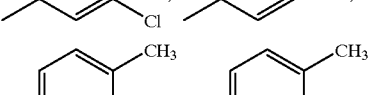

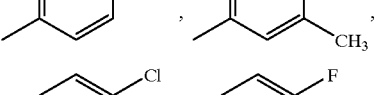

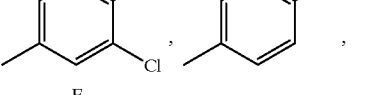

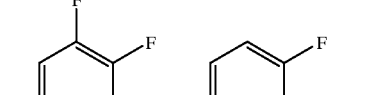

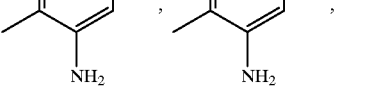

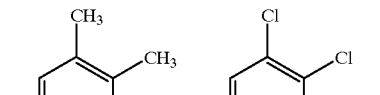

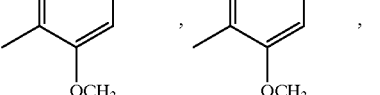

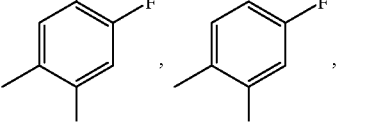

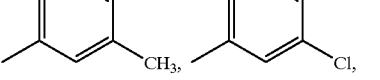

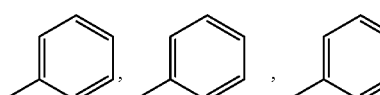

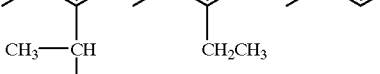

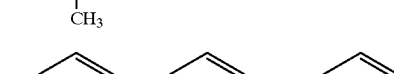

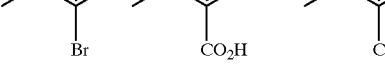

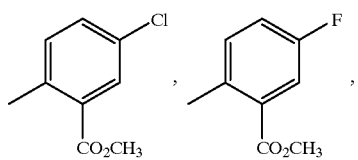
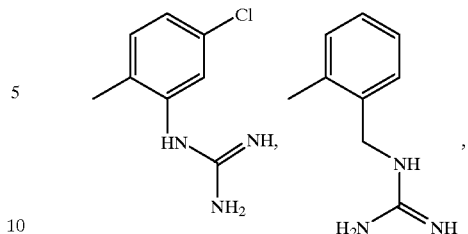
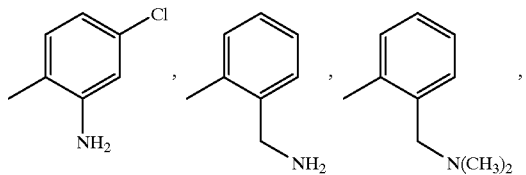
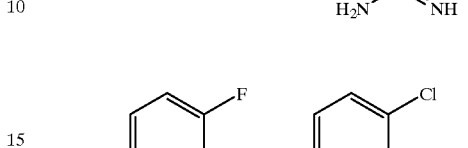
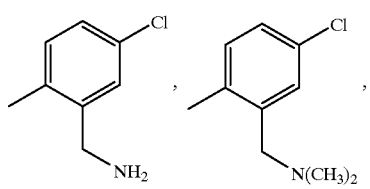
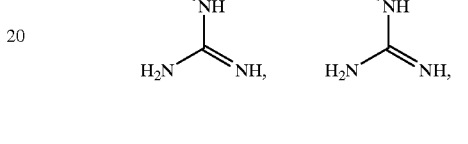
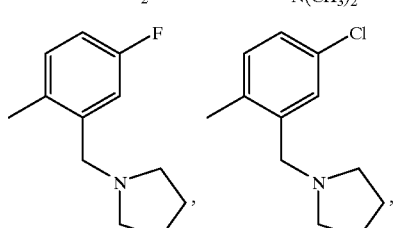
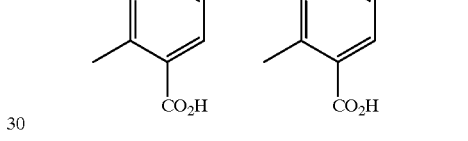
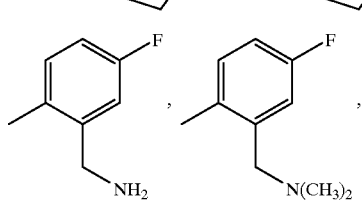
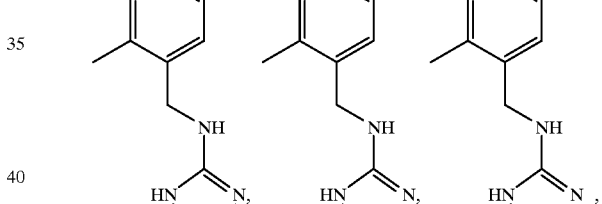
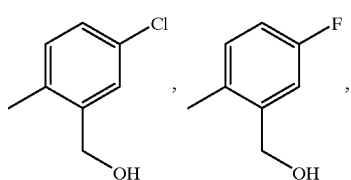
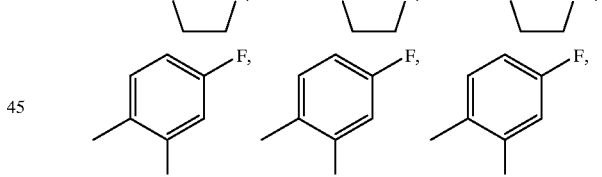
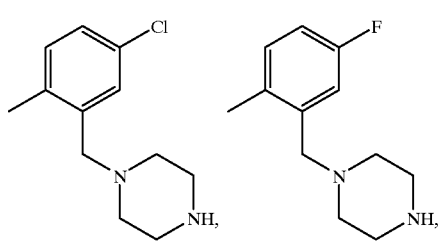
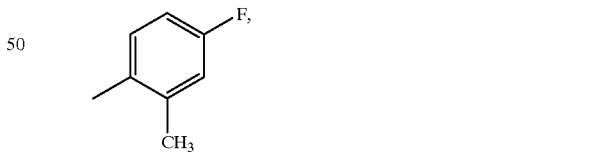
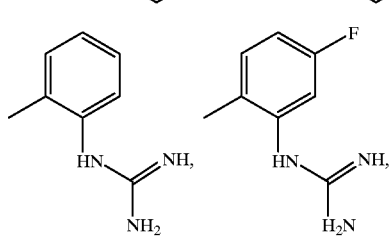

unsubstituted 2-pyridyl or unsubstituted phenyl.

Most preferred are compounds wherein $Q_2$ is selected from phenyl; 2-isopropylphenyl; 3,4-dimethylphenyl; 2-ethylphenyl; 3-fluorophenyl; 2-methylphenyl; 3-chloro-4-fluorophenyl; 3-chlorophenyl; 2-carbomethoxyphenyl; 2-carboxyphenyl; 2-methyl-4-chlorophenyl; 2-bromophenyl; 2-pyridyl; 2-methylenehydroxyphenyl; 4-fluorophenyl; 2-methyl-4-fluorophenyl; 2-chloro-4-fluorphenyl; 2,4-difluorophenyl; 2-hydroxy-4-fluorophenyl or 2-methylenehydroxy-4-fluorophenyl.

Some preferred embodiments are provided in Tables 1 to 3 below:
TABLE 1
Formula I compounds: X = S
| cmpd # | structure |
|---|---|
| 1 | 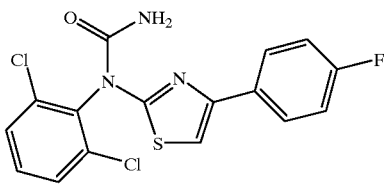 |
| 2 | 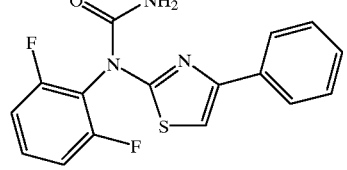 |
| 3 | 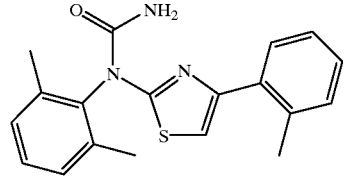 |
| 4 | 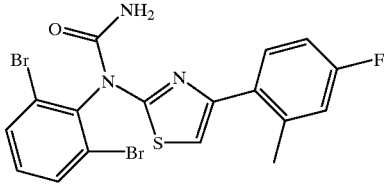 |
| 5 | 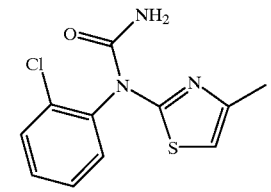 |
| 6 | 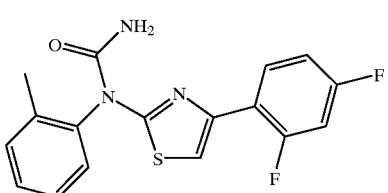 |
| 7 | 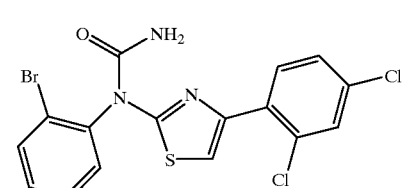 |
TABLE 1-continued
Formula I compounds: X = S
| cmpd # | structure |
|---|---|
| 8 | 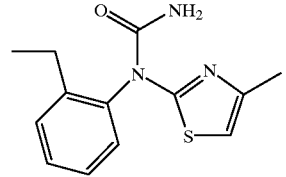 |
| 9 | 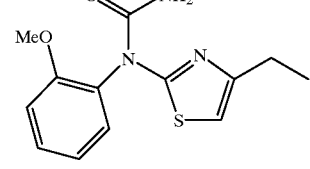 |
| 10 | 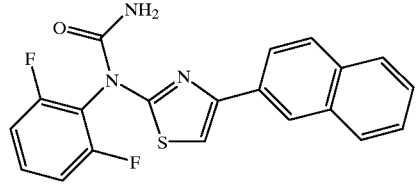 |
| 11 | 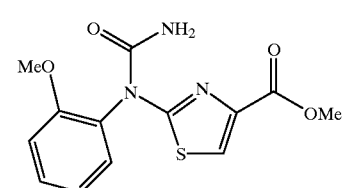 |
| 12 | 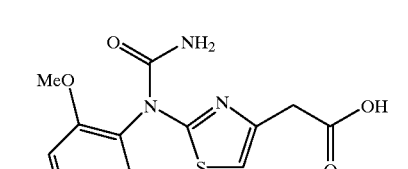 |
TABLE 2
Formula I compounds: X = O
| cmpd # | structure |
|---|---|
| 13 | 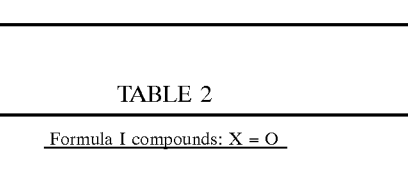 |

TABLE 2-continued
Formula I compounds: X = O
| cmpd # | structure |
|---|---|
| 14 | 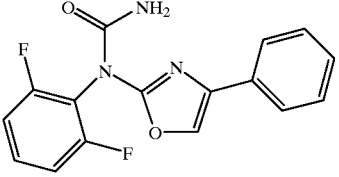 |
| 15 | 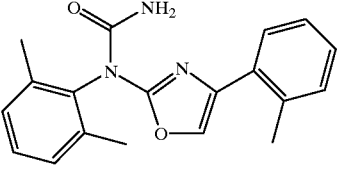 |
| 16 | 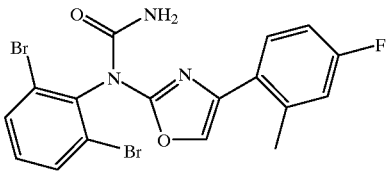 |
| 17 | 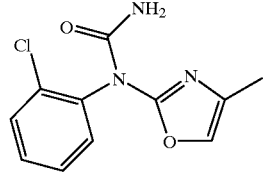 |
| 18 | 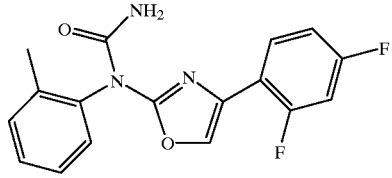 |
| 19 | 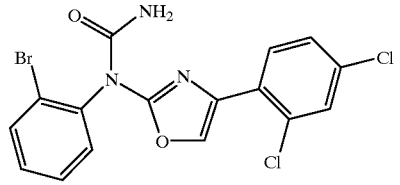 |
| 20 | 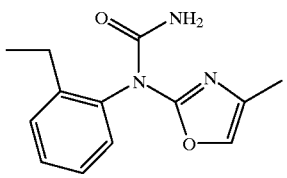 |
TABLE 2-continued
Formula I compounds: X = O
| cmpd # | structure |
|---|---|
| 21 | 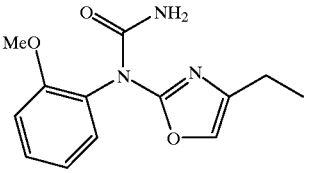 |
| 22 | 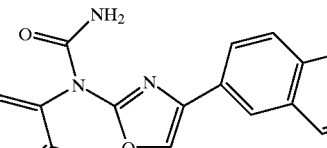 |
| 23 | 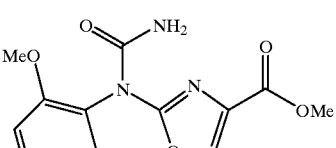 |
| 24 | 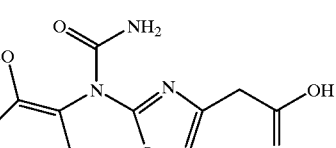 |
TABLE 3
Formula I compounds: X = NR
| cmpd # | structure |
|---|---|
| 25 | 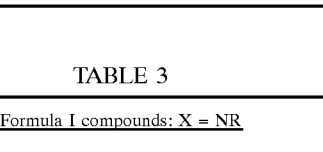 |
| 26 | 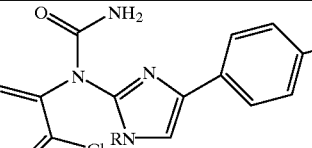 |
| 27 | 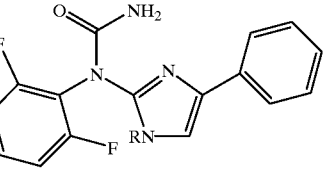 |

TABLE 3-continued

Formula I compounds: X = NR

| cmpd # | structure |
|---|---|
| 28 | (2,6-dibromophenyl)(4-(4-fluoro-2-methylphenyl)imidazol-2-yl) urea |
| 29 | (2-chlorophenyl)(4-methylimidazol-2-yl) urea |
| 30 | (2-methylphenyl)(4-(2,4-difluorophenyl)imidazol-2-yl) urea |
| 31 | (2-bromophenyl)(4-(2,4-dichlorophenyl)imidazol-2-yl) urea |
| 32 | (2-ethylphenyl)(4-methylimidazol-2-yl) urea |
| 33 | (2-methoxyphenyl)(4-ethylimidazol-2-yl) urea |
| 34 | (2,6-difluorophenyl)(4-(naphth-2-yl)imidazol-2-yl) urea |
| 35 | (2-methoxyphenyl)(4-methoxycarbonyl-imidazol-2-yl) urea |
| 36 | (2-methoxyphenyl)(4-carboxymethyl-imidazol-2-yl) urea |

In another embodiment, compounds of the instant invention may be Jnk3 inhibitors. In a preferred embodiment for Jnk3 inhibitors, n is 1. Jnk3 inhibitors may be formulated into pharmaceutical compositions for administration to animals or humans. These compositions can be used for methods of treating Jnk3-mediated neurological diseases.

According to another embodiment, the present invention provides methods of producing the above-identified compounds of formulae I and II.

A representative full synthesis scheme for the inhibitors of this invention of formula I where Z is N, X is O, S, or NR, and Y is CR is depicted below:

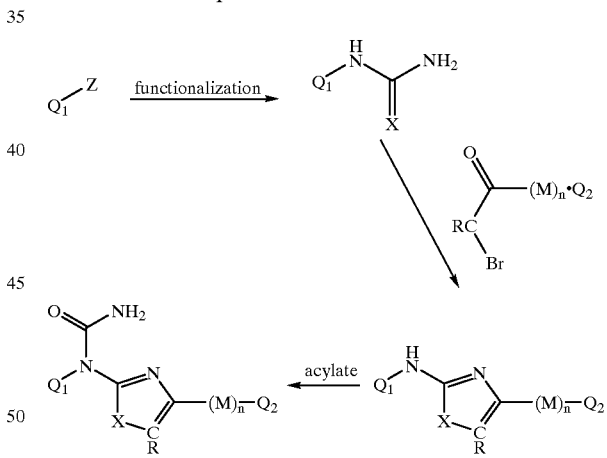

In step 1 of scheme 1, an aniline is converted to a urea, thiourea, or guanidine using, respectively, cyanic acid, thiocyanic acid, or 1H-pyrazole-1-carboxamidine. Alternatively, the three different functionalities can be obtained from any number of other reagents that are well known in the art. In step 2, the urea, thiourea, or guanidine is condensed with an (α-chloro or α-bromoketone in refluxing ethanol to obtain the oxazole, thiazole, or imidazole respectively. In step 3, the amine is acylated to provide the corresponding urea.

A similar synthesis scheme can be used for the production of compounds of formula II. In addition, other synthesis schemes known in the art can be used to produce the compounds of formulae I and II.

The activity of the p38 inhibitors of this invention may be assayed in vitro, in vivo or in a cell line. In vitro assays include assays that determine inhibition of either the kinase activity or ATPase activity of activated p38. Alternate in vitro assays quantitate the ability of the inhibitor to bind to p38 and may be measured either by radiolabelling the inhibitor prior to binding, isolating the inhibitor/p38 complex and determining the amount of radiolabel bound, or by running a competition experiment where new inhibitors are incubated with p38 bound to known radioligands.

Cell culture assays of the inhibitory effect of the compounds of this invention may be used to determine the amounts of TNF, IL-1, IL-6 or IL-8 produced in whole blood or cell fractions thereof in cells treated with inhibitor as compared to cells treated with negative controls. Level of these cytokines may be determined through the use of commercially available ELISAs.

An in vivo assay useful for determining the inhibitory activity of the p38 inhibitors of this invention is the suppression of hind paw edema in rats with *Mycobacterium butyricum*-induced adjuvant arthritis. This is described in J. C. Boehm et al., *J. Med. Chem.*, 39, pp. 3929–37 (1996), the disclosure of which is herein incorporated by reference. The p38 inhibitors of this invention may also be assayed in animal models of arthritis, bone resorption, endotoxin shock and immune function, as described in A. M. Badger et al., *J. Pharmacol. Experimental Therapeutics*, 279, pp. 1453–61 (1996), the disclosure of which is herein incorporated by reference.

The p38 inhibitors or pharmaceutical salts thereof may be formulated into pharmaceutical compositions for administration to animals or humans. These pharmaceutical compositions, which comprise an amount of p38 inhibitor effective to treat or prevent a p38-mediated condition and a pharmaceutically acceptable carrier, are another embodiment of the present invention.

The term "p38-mediated condition", as used herein means any disease or other deleterious condition in which p38 is known to play a role. This includes conditions caused by IL-1, TNF, IL-6 or IL-8 overproduction. Such conditions include, without limitation, inflammatory diseases, autoimmune diseases, destructive bone disorders, proliferative disorders, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2.

Inflammatory diseases which may be treated or prevented include, but are not limited to, acute pancreatitis, chronic pancreatitis, asthma, allergies, and adult respiratory distress syndrome.

Autoimmune diseases which may be treated or prevented include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, and graft vs. host disease.

Destructive bone disorders which may be treated or prevented include, but are not limited to, osteoporosis, osteoarthritis and multiple myeloma-related bone disorder.

Proliferative diseases which may be treated or prevented include, but are not limited to, acute myelogenous leukemia, chronic myelogenous leukemia, metastatic melanoma, Kaposi's sarcoma, and multiple myeloma.

Angiogenic disorders which may be treated or prevented include solid tumors, ocular neovasculization, infantile haemangiomas.

Infectious diseases which may be treated or prevented include, but are not limited to, sepsis, septic shock, and Shigellosis.

Viral diseases which may be treated or prevented include, but are not limited to, acute hepatitis infection (including hepatitis A, hepatitis B and hepatitis C), HIV infection and CMV retinitis.

Neurodegenerative and neurological diseases which may be treated or prevented by the compounds of this invention which inhibit p38 or Jnk3 include, but are not limited to, Alzheimer's disease, Parkinson's disease, cerebral ischemias, epilepsy or neurodegenerative disease caused by traumatic injury.

"p38-mediated conditions" also include ischemia/reperfusion in stroke, heart attacks, myocardial ischemia, organ hypoxia, vascular hyperplasia, cardiac hypertrophy, and thrombin-induced platelet aggregation.

In addition, p38 inhibitors in this invention are also capable of inhibiting the expression of inducible pro-inflammatory proteins such as prostaglandin endoperoxide synthase-2 (PGHS-2), also referred to as cyclooxygenase-2 (COX-2). Therefore, other "p38-mediated conditions" are edema, analgesia, fever and pain, such as neuromuscular pain, headache, pain caused by cancer, dental pain and arthritis pain.

The diseases that may be treated or prevented by the p38 inhibitors of this invention may also be conveniently grouped by the cytokine (IL-1, TNF, IL-6, IL-8) that is believed to be responsible for the disease.

Thus, an IL-1-mediated disease or condition includes rheumatoid arthritis, osteoarthritis, stroke, endotoxemia and/or toxic shock syndrome, inflammatory reaction induced by endotoxin, inflammatory bowel disease, tuberculosis, atherosclerosis, muscle degeneration, cachexia, psoriatic arthritis, Reiter's syndrome, gout, traumatic arthritis, rubella arthritis, acute synovitis, diabetes, pancreatic β-cell disease and Alzheimer's disease.

TNF-mediated diseases or conditions include rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis or pyresis. TNF-mediated diseases also include viral infections, such as HIV, CMV, influenza and herpes; and veterinary viral infections, such as lentivirus infections, including, but not limited to, equine infectious anemia virus, caprine arthritis virus, visna virus or maedi virus; or retrovirus infections, including feline immunodeficiency virus, bovine immunodeficiency virus, or canine immunodeficiency virus.

IL-8 mediated diseases or conditions include diseases characterized by massive neutrophil infiltration, such as psoriasis, inflammatory bowel disease, asthma, cardiac and renal reperfusion injury, adult respiratory distress syndrome, thrombosis and glomerulonephritis.

In addition, the compounds of this invention may be used topically to treat or prevent conditions caused or exacerbated by IL-1 or TNF. Such conditions include inflamed joints, eczema, psoriasis, inflammatory skin conditions such as sunburn, inflammatory eye conditions such as conjunctivitis, pyresis, pain, and other conditions associated with inflammation.

In addition to the compounds of this invention, pharmaceutically acceptable salts of the compounds of this invention may also be employed in compositions to treat or prevent the above-identified disorders.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium and potassium), alkaline earth metal (e.g., magnesium), ammonium and N–$(C_{1-4}$ alkyl)4+salts. This invention also envisions the quaternization of any basic nitrogen-containing groups of the compounds disclosed herein. Water or oil-soluble or dispersible products may be obtained by such quaternization.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of inhibitor that may be combined with the carrier materials to produce a single dosage form will vary depending upon the host treated, the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a p38-mediated condition comprising the step of administering to a patient one of the above-described pharmaceutical compositions. The term "patient", as used herein, means an animal, preferably a human.

Preferably, that method is used to treat or prevent a condition selected from inflammatory diseases, autoimmune diseases, destructive bone disorders, proliferative disorders, infectious diseases, degenerative diseases, allergies, reperfusion/ischemia in stroke, heart attacks, angiogenic disorders, organ hypoxia, vascular hyperplasia, cardiac hypertrophy, and thrombin-induced platelet aggregation.

According to another embodiment, the inhibitors of this invention are used to treat or prevent an IL-1, IL-6, IL-8 or TNF-mediated disease or condition. Such conditions are described above.

Depending upon the particular p38-mediated condition to be treated or prevented, additional drugs, which are normally administered to treat or prevent that condition may be administered together with the inhibitors of this invention. For example, chemotherapeutic agents or other antiproliferative agents may be combined with the p38 inhibitors of this invention to treat proliferative diseases.

Those additional agents may be administered separately, as part of a multiple dosage regimen, from the p38 inhibitor-containing composition. Alternatively, those agents may be part of a single dosage form, mixed together with the p38 inhibitor in a single composition.

In order that the invention described herein may be more fully understood, the following examples are set forth. It should be understood that these examples are for illustrative purposes only and are not to be construed as limiting this invention in any manner.

An example of the synthesis of a thiazole of formula I is set forth in the following example.

EXAMPLE 1

Synthesis of p38 Inhibitor Compound
A. Synthesis of the Thiourea

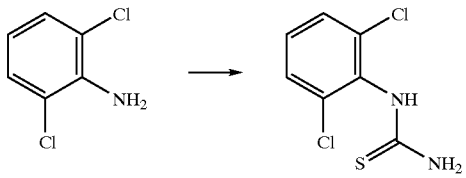

In a 250 mL round-bottomed flask, 9.95 g (60.2 mmol) of 2,6-dichloroaniline was dissolved in 50 mL of anhydrous $C_6H_6$. 8.0 g (82.3 mmol) of potassium isothiocyanate was added to the light brown solution of 2,6-dichloroaniline. 20 mL (130 mmol) trifluoroacetic acid was added, which produced an exotherm and a darkening of the mixture. The reaction was heated to reflux until the aniline was not observed by $CH_2Cl_2$ thin layer chromatography (TLC) analysis. The light yellow mixture was poured into $H_2O$ and extracted with $CH_2Cl_2$. The organic extract was dried in $MgSO_4$ and filtered over a plug of silica gel. The plug was eluted with $CH_2Cl_2$ to remove a small amount of nonpolar impurities. An elution with 25% EtOAc in $CH_2Cl_2$ and evaporation of the filtrate in vacuo produced 8.12 g, a 61% yield, of the thiourea as a clear, colorless oil.

B. Synthesis of the Thiazole

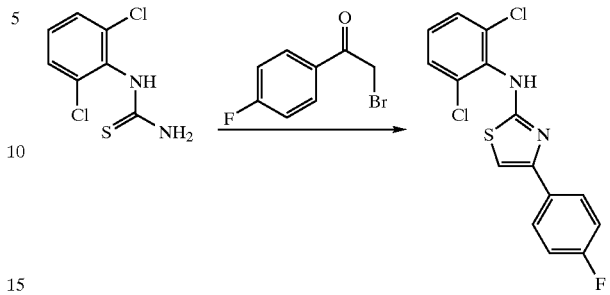

In a 100 mL round-bottomed flask, 1.04 g (4.70 mmol) of 2,6-dichlorophenyl thiourea made in Example 1A was dissolved in 25 mL of EtOH. 1.01 g (4.51 mmol) of commercially available 2-bromo-4'-fluoroacetophenone was added to the clear colorless solution of thiourea. The solution was heated to reflux until the starting materials were not observed by TLC ($CH_2Cl_2$) analysis. The light yellow liquid was cooled and the solvent was evaporated in vacuo to afford a yellow solid. The material was recrystallized from 1,2-dichloroethane-acetone to afford 1.06 g, a 70% yield, of the thiazole as a white solid.

C. Synthesis of the Urea

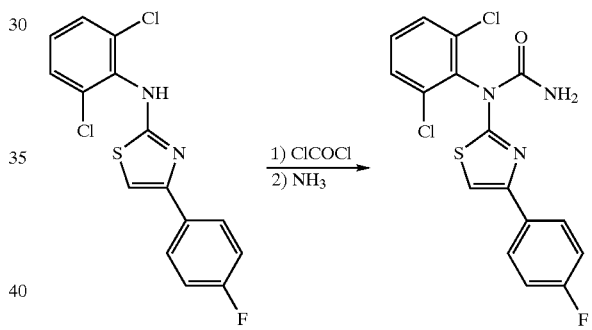

In a 25 mL round-bottomed flask, 371.4 mg (1.09 mmol) of the thiourea produced in example 1B was dissolved in 7 mL of 20% w/w phosgene in toluene. The suspension was heated to reflux until all of the solid thiourea was dissolved. The solution was cooled and 5 mL of 2.0M $NH_3$ in MeOH was added, which precipitated a white solid. The mixture was stirred overnight, poured into water and extracted with $CH_2Cl_2$. The organic extract was dried in $MgSO_4$ and evaporated in vacuo to afford the urea as a white solid.

EXAMPLE 2

Cloning of p38 Kinase in Insect Cells

Two splice variants of human p38 kinase, CSBP1 and CSBP2, have been identified. Specific oligonucleotide primers were used to amplify the coding region of CSBP2 cDNA using a HeLa cell library (Stratagene) as a template. The polymerase chain reaction product was cloned into the pET-15b vector (Novagen). The baculovirus transfer vector, pVL-(His)6-p38 was constructed by subcloning a XbaI-BamHI fragment of pET15b-(His)6–p38 into the complementary sites in plasmid pVL1392 (Pharmingen).

The plasmid pVL-(His)6–p38 directed the synthesis of a recombinant protein consisting of a 23-residue peptide (MGSSHHHHHHSSGLVPRGSHMLE, where LVPRGS represents a thrombin cleavage site) fused in frame to the N-terminus of p38, as confirmed by DNA sequencing and by N-terminal sequencing of the expressed protein. Monolayer culture of Spodoptera frugiperda (Sf9) insect cells (ATCC) was maintained in TNM-FH medium (Gibco BRL) supplemented with 10% fetal bovine serum in a T-flask at 27° C. Sf9 cells in log phase were co-transfected with linear viral DNA of Autographa califonica nuclear polyhedrosis virus (Pharmingen) and transfer vector pVL-(His) 6–p38 using Lipofectin (Invitrogen). The individual recombinant baculovirus clones were purified by plaque assay using 1% low melting agarose.

EXAMPLE 3

Expression and Purification of Recombinant p38 Kinase

Trichoplusia ni (Tn-368) High-Five™ cells (Invitrogen) were grown in suspension in Excel-405 protein free medium (JRH Bioscience) in a shaker flask at 27° C. Cells at a density of $1.5 \times 10^6$ cells/ml were infected with the recombinant baculovirus described above at a multiplicity of infection of 5. The expression level of recombinant p38 was monitored by immunoblotting using a rabbit anti-p38 antibody (Santa Cruz Biotechnology). The cell mass was harvested 72 hours after infection when the expression level of p38 reached its maximum.

Frozen cell paste from cells expressing the $(His)_6$-tagged p38 was thawed in 5 volumes of Buffer A (50 mM NaH2PO4 pH 8.0, 200 mM NaCl, 2mM β-Mercaptoethanol, 10% Glycerol and 0.2 mM PMSF). After mechanical disruption of the cells in a microfluidizer, the lysate was centrifuged at 30,000×g for 30 minutes. The supernatant was incubated batchwise for 3–5 hours at 4° C. with Talon™ (Clontech) metal affinity resin at a ratio of 1 ml of resin per 2–4 mgs of expected p38. The resin was settled by centrifugation at 500×g for 5 minutes and gently washed batchwise with Buffer A. The resin was slurried and poured into a column (approx. 2.6×5.0 cm) and washed with Buffer A+5 mM imidazole.

The $(His)_6$–p38 was eluted with Buffer A+100 mM imidazole and subsequently dialyzed overnight at 4° C. against 2 liters of Buffer B, (50 mM HEPES, pH 7.5, 25 mM β-glycerophosphate, 5% glycerol, 2mM DTT). The $His_6$ tag was removed by addition of at 1.5 units thrombin (Calbiochem) per mg of p38 and incubation at 20° C. for 2–3 hours. The thrombin was quenched by addition of 0.2 mM PMSF and then the entire sample was loaded onto a 2 ml benzamidine agarose (American International Chemical) column.

The flow through fraction was directly loaded onto a 2.6×5.0 cm Q-Sepharose (Pharmacia) column previously equilibrated in Buffer B+0.2 mM PMSF. The p38 was eluted with a 20 column volume linear gradient to 0.6M NaCl in Buffer B. The eluted protein peak was pooled and dialyzed overnight at 4° C. vs. Buffer C (50 mM HEPES pH 7.5, 5% glycerol, 50 mM NaCl, 2 mM DTT, 0.2 mM PMSF).

The dialyzed protein was concentrated in a Centriprep (Amicon) to 3–4 ml and applied to a 2.6×100 cm Sephacryl S-100HR (Pharmacia) column. The protein was eluted at a flow rate of 35 ml/hr. The main peak was pooled, adjusted to 20 mM DTT, concentrated to 10–80 mgs/ml and frozen in aliquots at −70° C. or used immediately.

EXAMPLE 4

Activation of p38 p38 was activated by combining 0.5 mg/ml p38 with 0.005 mg/ml DD-double mutant MKK6 in Buffer B+10 mM MgCl2, 2 mM ATP, 0.2 mM Na2VO4 for 30 minutes at 20° C. The activation mixture was then loaded onto a 1.0×10 cm MonoQ column (Pharmacia) and eluted with a linear 20 column volume gradient to 1.0 M NaCl in Buffer B. The activated p38 eluted after the ADP and ATP. The activated p38 peak was pooled and dialyzed against buffer B+0.2 mM Na2VO4 to remove the NaCl. The dialyzed protein was adjusted to 1.1M potassium phosphate by addition of a 4.0M stock solution and loaded onto a 1.0×10 cm HIC (Rainin Hydropore) column previously equilibrated in Buffer D (10% glycerol, 20 mM β-glycerophosphate, 2.0 mM DTT)+1.1MK2HPO4. The protein was eluted with a 20 column volume linear gradient to Buffer D +50 mM K2HPO4. The double phosphorylated p38 eluted as the main peak and was pooled for dialysis against Buffer B+0.2mM Na2VO4. The activated p38 was stored at −70° C.

EXAMPLE 5

P38 Inhibition Assays

A. Inhibition of Phosphorylation of EGF Receptor Peptide

This assay is carried out in the presence of 10 mM MgCl2, 25 mM β-glycerophosphate, 10% glycerol and 100 mM HEPES buffer at pH 7.6. For a typical IC50 determination, a stock solution is prepared containing all of the above components and activated p38 (5 nM). The stock solution is aliquotted into vials. A fixed volume of DMSO or inhibitor in DMSO (final concentration of DMSO in reaction is 5%) is introduced to each vial, mixed and incubated for 15 minutes at room temperature. EGF receptor peptide, KRELVEPLTPSGEAPNQALLR, a phosphoryl acceptor in p38-catalyzed kinase reaction, is added to each vial to a final concentration of 200 μM. The kinase reaction is initiated with ATP (100 μM) and the vials are incubated at 30 ° C. After 30 minutes, the reactions are quenched with equal volume of 10% trifluoroacetic acid (TFA).

The phosphorylated peptide is quantified by HPLC analysis. Separation of phosphorylated peptide from the unphosphorylated peptide is achieved on a reverse phase column (Deltapak, 5 μm, C18 100D, part no. 011795) with a binary gradient of water and acteonitrile, each containing 0.1% TFA. IC50 (concentration of inhibitor yielding 50% inhibition) is determined by plotting the % activity remaining against inhibitor concentration.

B. Inhibition of ATPase Activity

This assay is carried out in the presence of 10 mM MgCl2, 25 mM β-glycerophosphate, 10% glycerol and 100 mM HEPES buffer at pH 7.6. For a typical Ki determination, the Km for ATP in the ATPase activity of activated p38 reaction is determined in the absence of inhibitor and in the presence of two concentrations of inhibitor. Ki is determined from the rate data as a function of inhibitor and ATP concentrations. A stock solution is prepared containing all of the above components and activated p38 (60 nM). The stock solution is aliquotted into vials. A fixed volume of DMSO or inhibitor in DMSO (final concentration of DMSO in reaction is 2.5%) is introduced to each vial, mixed and incubated for 15 minutes at room temperature. The reaction is initiated by adding various concentrations of ATP and then incubated at 30° C. After 30 minutes, the reactions are quenched with 50 μl of EDTA (0.1 M, final concentration), pH 8.0. The product of p38 ATPase activity, ADP, is quantified by HPLC analysis.

Separation of ADP from ATP is achieved on a reversed phase column (Supelcosil, LC-18, 3 μm, part no. 5–8985) using a binary solvent gradient of following composition: Solvent A-0.1 M phosphate buffer containing 8 mM tetrabutylammonium hydrogen sulfate (Sigma Chemical Co., catalogue no. T-7158), Solvent B-Solvent A with 30% methanol.

C. Inhibition of IL-1, TNF, IL-6 and IL-8 Production in LPS-Stimulated PBMCs

Inhibitors are serially diluted in DMSO from a 20 mM stock. At least 6 serial dilutions are prepared. Then 4× inhibitor stocks are prepared by adding 4 μl of an inhibitor dilution to 1 ml of RPMI1640 medium/10% fetal bovine serum. The 4× inhibitor stocks contained inhibitor at concentrations of 80 μM, 32 μM, 12.8 μM, 5.12 μM, 2.048 μM, 0.819 μM, 0.328 μM, 0.131 μM, 0.052 μM, 0.021 μM etc. The 4× inhibitor stocks are pre-warmed at 37° C. until use.

Fresh human blood buffy cells are separated from other cells in a Vacutainer CPT from Becton & Dickinson (containing 4 ml blood and enough DPBS without $Mg^{2+}$/$Ca^{2+}$ to fill the tube) by centrifugation at 1500×g for 15 min. Peripheral blood mononuclear cells (PBMCs), which are located on top of the gradient in the Vacutainer, are removed and washed twice with RPMI1640 medium/10% fetal bovine serum. PBMCs are collected by centrifugation at 500×g for 10 min. The total cell number is determined using a Neubauer Cell Chamber and the cells are adjusted to a concentration of $4.8 \times 10^6$ cells/ml in cell culture medium (RPMI1640 supplemented with 10% fetal bovine serum).

Alternatively, whole blood containing an anti-coagulant is used directly in the assay.

100 μl of cell suspension or whole blood is placed in each well of a 96-well cell culture plate. Then, 50 μl of the 4×inhibitor stock to the cells is added. Finally, 50 μl of a lipopolysaccharide (LPS) working stock solution (16 ng/ml in cell culture medium) is added to give a final concentration of 4 ng/ml LPS in the assay. The total assay volume of the vehicle control is also adjusted to 200 μl by adding 50 μl cell culture medium. The PBMC cells or whole blood are then incubated overnight (for 12–15 hours) at 37° C./5% CO2 in a humidified atmosphere.

The next day the cells are mixed on a shaker for 3–5 minutes before centrifugation at 500×g for 5 minutes. Cell culture supernatants are harvested and analyzed by ELISA for levels of IL-1b (R & D Systems, Quantikine kits, #DBL50), TNF-α (BioSource, #KHC3012), IL-6 (Endogen, #EH2-IL6) and IL-8 (Endogen, #EH2-IL8) according to the instructions of the manufacturer. The ELISA data are used to generate dose-response curves from which IC50 values are derived. p38 inhibitors of this invention will inhibit phosphorylation of EGF receptor peptide, and the production of IL-1, TNF and IL-6, as well as IL-8 in LPS-stimulated PBMCs or in whole blood.

D. Inhibition of IL-6 and IL-8 Production in IL-1-Stimulated PBMCs

This assay is carried out on PBMCs exactly the same as above except that 50 μl of an IL-1b working stock solution (2 ng/ml in cell culture medium) is added to the assay instead of the (LPS) working stock solution.

Cell culture supernatants are harvested as described above and analyzed by ELISA for levels of IL-6 (Endogen, #EH2-IL6) and IL-8 (Endogen, #EH2-IL8) according to the instructions of the manufacturer. The ELISA data are used to generate dose-response curves from which IC50 values are derived.

E. Inhibition of LPS-Induced Prostaglandin Endoperoxide Synthase-2 (PGHS-2, or COX-2) Induction In PBMCs Human peripheral mononuclear cells (PBMCs) are isolated from fresh human blood buffy coats by centrifugation in a Vacutainer CPT (Becton & Dickinson). $15 \times 10^6$ cells are seeded in a 6-well tissue culture dish containing RPMI 1640 supplemented with 10% fetal bovine serum, 50 U/ml penicillin, 50 μg/ml streptomycin, and 2 mM L-glutamine. An inhibitor of the instant invention is added at 0.2, 2.0 and 20 μM final concentrations in DMSO. Then, LPS is added at a final concentration of 4 ng/ml to induce enzyme expression. The final culture volume is 10 ml/well.

After overnight incubation at 37° C., 5% $CO_2$, the cells are harvested by scraping and subsequent centrifugation, then the supernatant is removed, and the cells are washed twice in ice-cold DPBS (Dulbecco's phosphate buffered saline, BioWhittaker). The cells are lysed on ice for 10 min in 50 μl cold lysis buffer (20 mM Tris-HCl, pH 7.2, 150 mM NaCl, 1% Triton-X-100, 1% deoxycholic acid, 0.1% SDS, 1 mM EDTA, 2% aprotinin (Sigma), 10 μg/ml pepstatin, 10 μg/ml leupeptin, 2 mM PMSF, 1 mM benzamidine, 1 mM DTT) containing 1 μl Benzonase (DNAse from Merck). The protein concentration of each sample is determined using the BCA assay (Pierce) and bovine serum albumin as a standard. Then the protein concentration of each sample is adjusted to 1 mg/ml with cold lysis buffer. To 100 μl lysate an equal volume of 2×SDS PAGE loading buffer is added and the sample is boiled for 5 min. Proteins (30 μg/lane) are size-fractionated on 4–20% SDS PAGE gradient gels (Novex) and subsequently transferred onto nitrocellulose membrane by electrophoretic means for 2 hours at 100 mA in Towbin transfer buffer (25 mM Tris, 192 mM glycine) containing 20% methanol. The membrane is pretreated for 1 hour at room temperature with blocking buffer (5% non-fat dry milk in DPBS supplemented with 0.1% Tween-20) and washed 3 times in DPBS/0.1% Tween-20. The membrane is incubated overnight at 4° C. with a 1:250 dilution of monoclonal anti-COX-2 antibody (Transduction Laboratories) in blocking buffer. After 3 washes in DPBS/0.1% Tween-20, the membrane is incubated with a 1:1000 dilution of horseradish peroxidase-conjugated sheep antiserum to mouse Ig (Amersham) in blocking buffer for 1 h at room temperature. Then the membrane is washed again 3 times in DPBS/0.1% Tween-20 and an ECL detection system (SuperSignal™ CL-HRP Substrate System, Pierce) is used to determine the levels of expression of COX-2.

While we have hereinbefore presented a number of embodiments of this invention, it is apparent that our basic construction can be altered to provide other embodiments which utilize the methods of this invention.

We claim:

1. A compound having the formula:

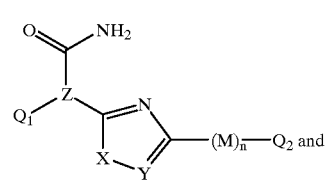

I

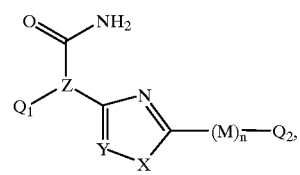

II wherein:
each of $Q_1$ and $Q_2$ is independently selected from the group consisting of a 5–6 membered aromatic carbocyclic or heterocyclic ring system, and an 8–10 membered bicyclic ring system comprising aromatic carbocyclic rings, aromatic heterocyclic rings or a combination of an aromatic carbocyclic ring and an aromatic heterocyclic ring; or wherein:

$Q_1$ is selected from the group consisting of a 5–6 membered aromatic carbocyclic or heterocyclic ring systam and an 8–10 membered bicyclic ring system comprising aromatic carbocyclic rings, aromatic heterocyclic rings or a combination of an aromatic carbocyclic ring and an aromatic heterocyclic ring, and $Q_2$ is selected from the group consisting of H, $CO_2R'$, $CON(R')_2$, and a $(C_1-C_4)$ branched or straight-chain alkyl optionally containing 1–3 substituents independently selected from the group consisting of A, T—C(O)R', $OPO_3H_2$, $NR'_2$, OR', $CO_2R'$, $CON(R')_2$, and $SO_2N(R^2)_2$;

wherein:

$Q_1$ is optionally substituted with 1 to 4 substituents, each of which is independently selected from the group consisting of halo; $C_1-C_4$ alkyl optionally containing 1–3 substituents independently selected from the group consisting of A, T—C(O)R', $OPO_3H_2$, $NR'_2$, OR', $CO_2R'$ and $CONR'_2$; O—$(C_1-C_4)$-alkyl optionally containing 1–3 substituents independently selected from the group consisting of A, T—C(O)R', $OPO_3H_2$, $NR'_2$, OR', $CO_2R'$ and $CONR'_2$; $NR'_2$; $OCF_3$; $CF_3$; $NO_2$; $CO_2R'$; CONR'; SR'; $S(O_2)N(R')_2$; $SCF_3$; CN; $N(R')C(O)R^4$; $N(R')C(O)OR^4$; $N(R')C(O)C(O)R^4$; $N(R')S(O_2)R^4$; $N(R')R^4$; $N(R^4)_2$; $OR^4$; $OC(O)R^4$; $OP(O)_3H_2$; and N=C—$N(R')_2$; and wherein:

$Q_2$, when a ring system, is optionally substituted with up to 4 substituents, each of which is independently selected from the group consisting of halo; $C_1-C_4$ straight or branched alkyl optionally containing 1–3 substituents independently selectd from the group consisting of A, T—C(O)R', $OPO_3H_2$, $NR'_2$, OR', $CO_2R'$, $S(O_2)N(R')_2$, N=C—$N(R')_2$, $R^3$, and $CONR'_2$; O—$(C_1-C_3)$-alkyl; O—$(c_1-C_4)$-alkyl optionally containing 1–3 substituents independently selected from the group consisting of A, T—C(O)R', $OPO_3H_2$, $NR'_2$, OR', $CO_2R'$, $S(O_2)N(R')_2$, N=C-N$(R')_2$, $R^3$, and $CONR'_2$; $OCF_3$; $CF_3$, $NO_2$; $CO_2R'$; CONR'; $R^3$; $OR^3$; $NR^3$; $SR^3$; $C(O)R^3$; $C(O)N(R')R^3$; $C(O)OR^3$; SR'; $S(O_2)N(R')_2$; $SCF_3$; N=C—$N(R')_2$; and CN;

wherein A is selected from the group consisting of;

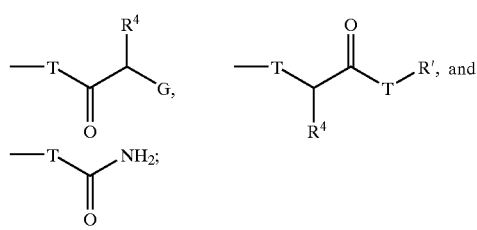

T is either O or NH; and
G is either $NH_2$ or OH;

wherein R' is selected from the group consisting of hydrogen, $(C_1-C_3)$-alkyl; $(C_2-C_3)$-alkenyl or alkynyl; and phenyl or phenyl substituted with 1 to 3 substituents independently selected from the group consisting of halo, methoxy, cyano, nitro, amino, hydroxy, methyl and ethyl;

wherein $R^3$ is a 5–6 membered aromatic carbocyclic or heterocyclic ring system;

wherein $R^4$ is $(C_1-C_4)$-alkyl optionally substituted with $N(R')_2$, OR', $CO_2R'$, $CON(R')_2$, or $SO_2N(R^2)_2$; a 5–6 membered carbocyclic or heterocyclic ring system optionally substituted with a $(C_1-C_4)$ branched or straight-chain alkyl group, $N(R')_2$, OR', $CO_2R'$, $CON(R')_2$, or $SO_2N(R^2)_2$; or a $(C_1-C_4)$-alkyl optionally substituted with the 5–6 membered carbocyclic or heterocyclic ring system optionally substituted with a $(C_1-C_4)$ branched or straight-chain alkyl group, $N(R')_2$, OR', $CO_2R'$, $CON(R')_2$, or $SO_2N(R^2)_2$;

wherein $R_2$ is selected from the group consisting of hydrogen, $(C_1-C_3)$-alkyl, and $(C_1-C_3)$-alkenyl; each optionally substituted with —$N(R')_2$, —OR', SR', —C(O)—$N(R')_2$, —$S(O_2)$—$N(R')_2$, —C(O)—OR', or $R^3$;

wherein X is selected from the group consisting of O, S, NR and $C(R)_2$;

wherein Y is CR or N;

wherein Z is CH or N;

wherein M is C=O, CHOH, or $CH_2$;

wherein n is 0 or 1;

wherein each R is independently selected from the group consisting of hydrogen —$R^2$, —$N(R^2)_2$, —$OR^2$, $SR^2$, —C(O)—$N(R^2)_2$, —$S(O_2)$—$N(R^2)_2$, and —C(O)—$OR^2$, wherein two adjacent R are optionally bound to one another and, together with each Y to which they are respectively bound, form a 4–8 membered carbocyclic or heterocyclic ring;

and pharmaceutically acceptable salts thereof;

wherein when $Q_1$ is substituted with 1 to 3 substituents, $Q_2$ is a ring system, X is NR or $C(R)_2$, and n is 1, then M is not —C(O)— or —$CH_2$—; when Y is N and/or X is NR, Z is CH, n is 0 and $Q_1$ is a substituted or unsubstituted phenyl or thienyl group, then $Q_2$ is not H; and when Y is CH, X is S, Z is CH, and n is 0, then $Q_2$ is not H.

2. The compound according to claim 1, wherein $Q_1$ is selected from the group consisting of phenyl and pyridyl, wherein said phenyl and pyridyl contain 1 to 3 substituents independently selected from the group consisting of chloro, fluoro, bromo, —$CH_3$, —$OCH_3$, —OH, —$CF_3$, —$OCF_3$, —$O(CH_2)_2CH_3$, $NH_2$—, 3,4-*methylenedioxy*, —$N(CH3)_2$, —NH—$S(O)_2$-phenyl, —NH—C(O)O—$CH_2$-4-pyridine, —NH—C(O)$CH_2$-morpholine, —NH—C(O)$CH_2$—$N(CH_3)_2$, —NH—C(O)$CH_2$-piperazine, —NH—c(O)$CH_2$-pyrrolidine, —NH—C(O)C(O)-morpholine, —NH—C(O)C(O)-piperazine, —NH—C(O)C(O)-pyrrolidine, —O—C(O)$CH_2$—$N(CH_3)_2$, and —O—$(CH_2)_2$—$N(CH_3)_2$, and wherein at least one of said substituents is in the ortho position.

3. The compound according to claim 2, wherein $Q_1$ contains at least two substituents, both of which are in the ortho position.

4. The compound according to claim 2, wherein $Q_1$ is selected from the group consisting of:

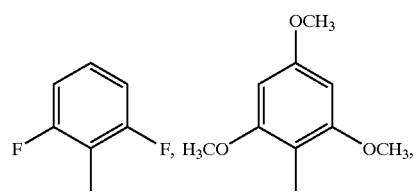

-continued
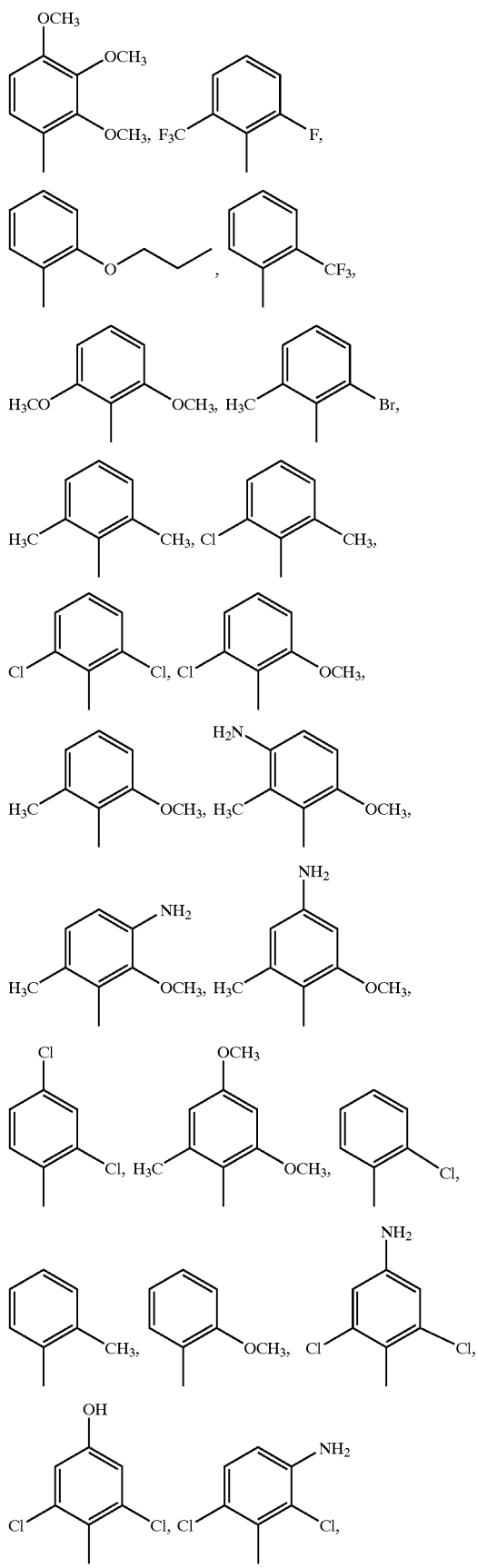
-continued
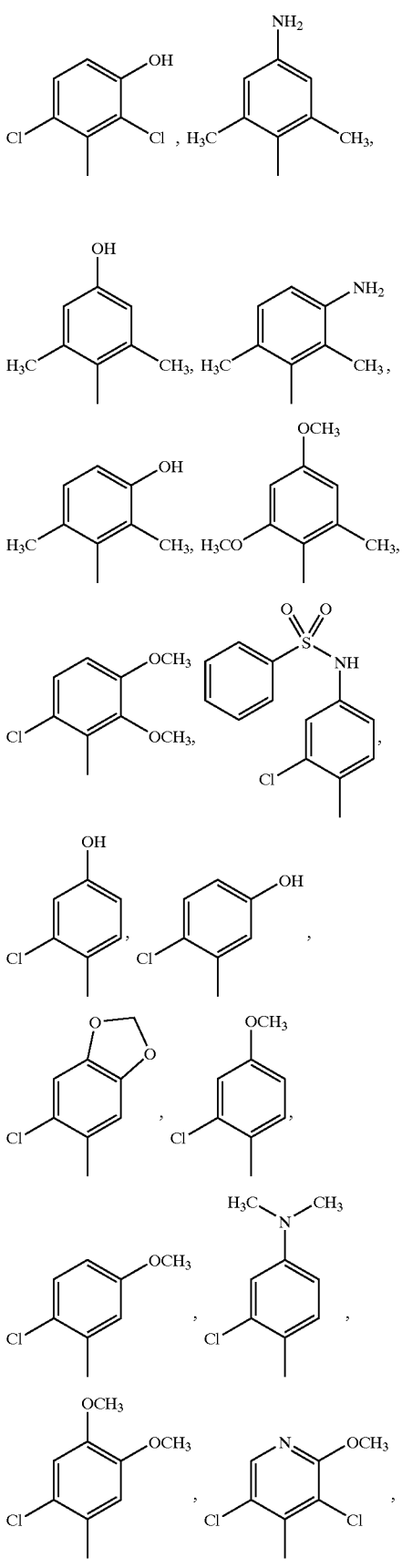

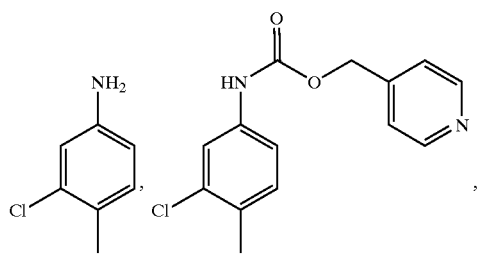
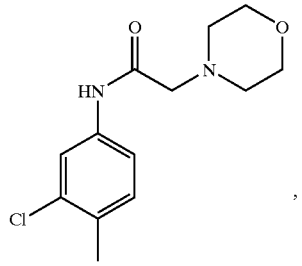
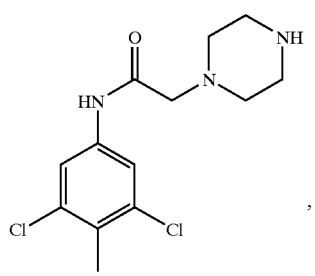
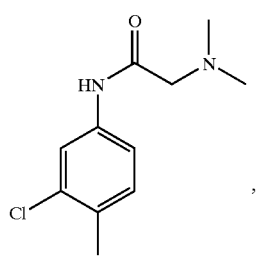
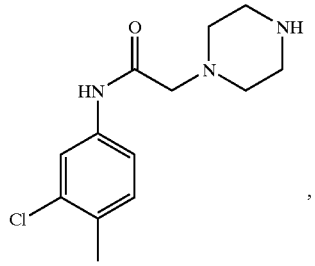
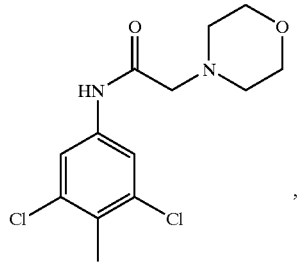
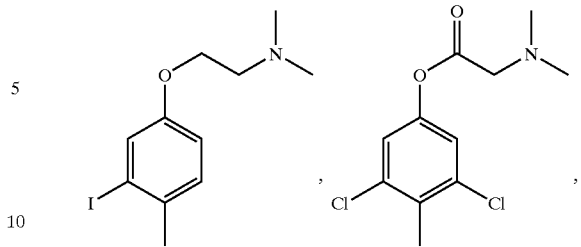
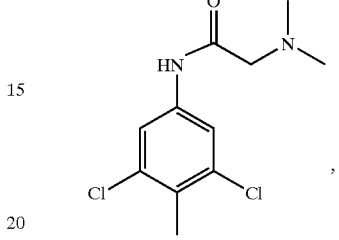
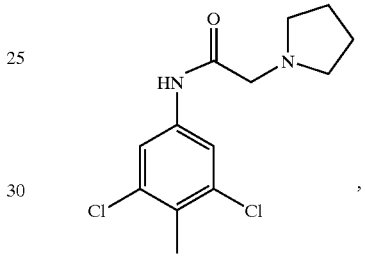
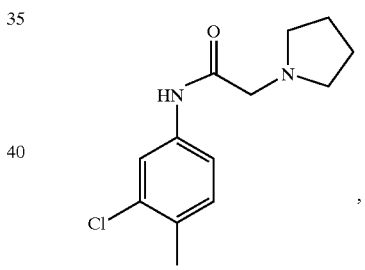
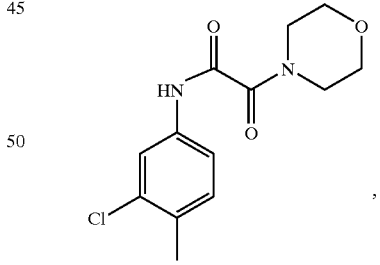
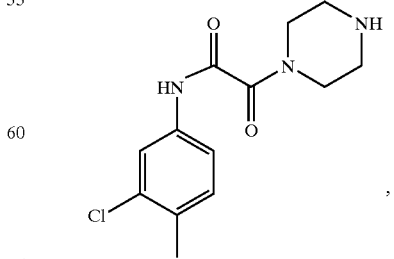

5. The compound according to claim 4, wherein $Q_1$ is selected from the group consisting of 2-fluoro-6-trifluoromethylphenyl; 2,6-difluorophenyl; 2,6-dichlorophenyl; 2-chloro-4-hydroxyphenyl; 2-chloro-4-aminophenyl; 2,6-dichloro-4-aminophenyl; 2,6-dichloro-3-aminophenyl; 2,6-dimethyl-4-hydroxyphenyl; 2-methoxy-3,5-dichloro-4-pyrido; 2-chloro-4,5 methylenedioxy phenyl and 2chloro-4-(N-2-morpholino-acetamido)phenyl.

6. The compound according to claim 1, wherein $Q_2$ is selected from the group consisting of phenyl and pyridyl, and wherein $Q_2$ optionally contains up to 3 substituents, each of which is independently selected from the group consisting of chloro, fluoro, bromo, methyl, ethyl, isopropyl, —OCH₃, —OH, —NH₂, —CF₃, —OCF₃, —SCH₃, —OCH₃, —C(O)OH, —C(O)OCH₃, —CH₂NH₂, —N(CH₃)₂, —CH₂-pyrrolidine and —CH₂OH.

7. The compound according to claim 6, wherein $Q_2$ is selected from the group consisting of:

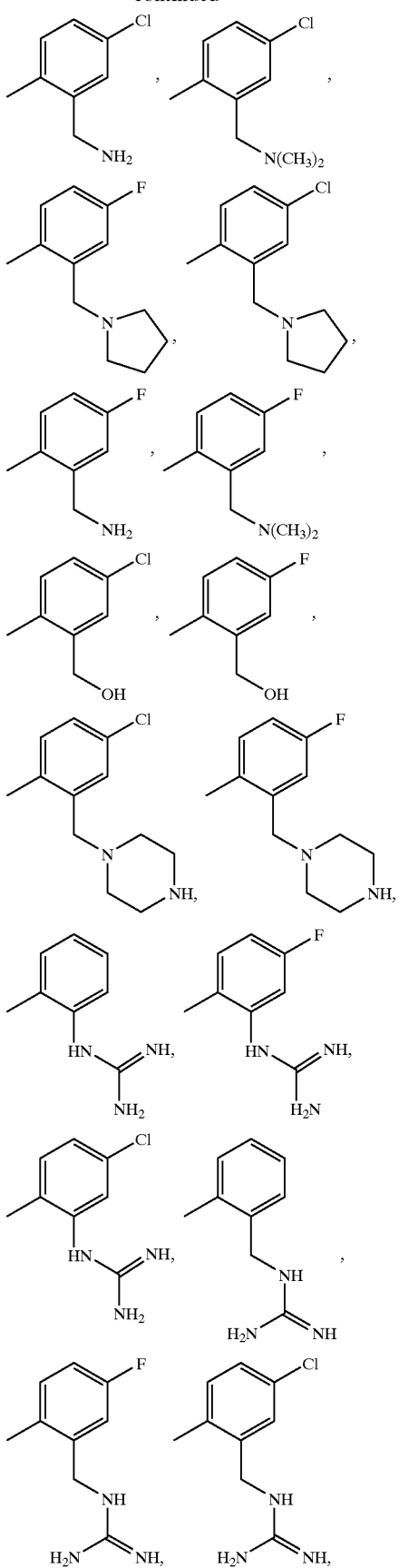

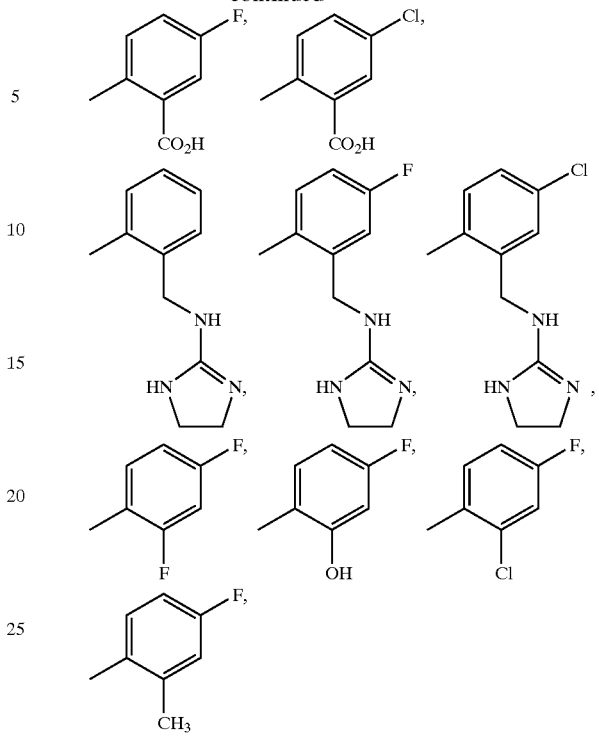

unsubstituted 2-pyridyl and unsubstituted phenyl.

8. The compound according to claim 7, wherein $Q_2$ is selected from the group consisting of phenyl; 2-isopropylphenyl; 3,4-dimethylphenyl; 2-ethylphenyl; 3-fluorophenyl; 2-methylphenyl; 3-chloro-4-fluorophenyl; 3-chlorophenyl; 2-carbomethoxyphenyl; 2-carboxyphenyl; 2-methyl-4-chlorophenyl; 2-bromophenyl; 2-pyridyl; 2-methylenehydroxyphenyl; 4-fluorophenyl; 2-methyl-4-fluorophenyl; 2-chloro-4-fluorophenyl; 2,4-difluorophenyl; 2-hydroxy-4-fluorophenyl and 2-methylenehydroxy-4-fluorophenyl.

9. The compound according to claim 1, wherein X is S.

10. The compound according to claim 1, wherein X is O.

11. The compound according to claim 1, wherein X is NR.

12. The compound according to claim 1, wherein Y is CR and wherein said R is H.

13. The compound according to claim 1, wherein said compound is any one compounds 1 to 12;

| cmpd # | structure |
|---|---|
| 1 | 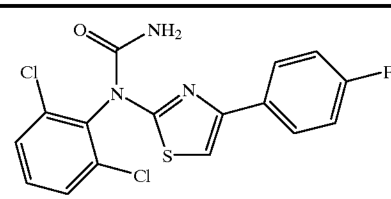 |

-continued
| cmpd # | structure |
|---|---|
| 2 | 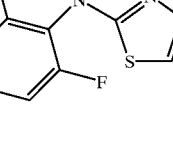 |
| 3 | 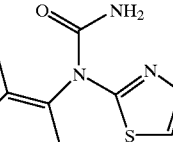 |
| 4 | 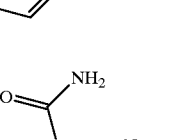 |
| 5 | 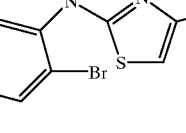 |
| 6 | 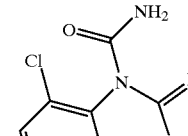 |
| 7 | 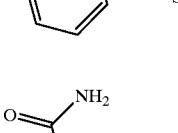 |
| 8 | 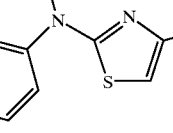 |
-continued
| cmpd # | structure |
|---|---|
| 9 | 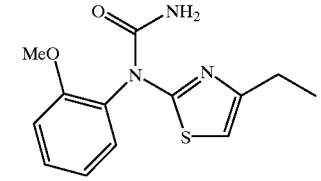 |
| 10 | 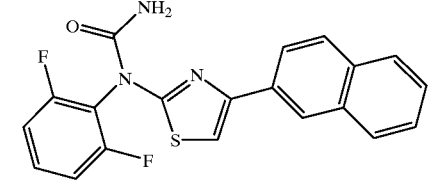 |
| 11 | 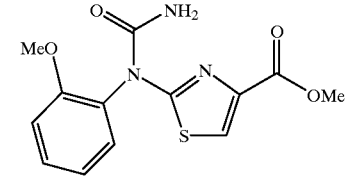 |
| 12 | 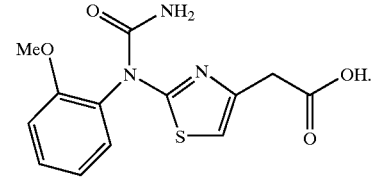 |
14. The compound according to claim 1, wherein ssaid compound is any one of compounds 13 to 24;
| cmpd # | structure |
|---|---|
| 13 | 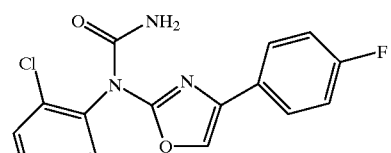 |
| 14 | 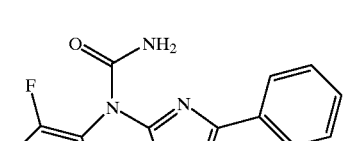 |

-continued

| cmpd # | structure |
|---|---|
| 15 | (2,6-dimethylphenyl)-[4-(2-methylphenyl)oxazol-2-yl]urea |
| 16 | (2,6-dibromophenyl)-[4-(4-fluoro-2-methylphenyl)oxazol-2-yl]urea |
| 17 | (2-chlorophenyl)-(4-methyloxazol-2-yl)urea |
| 18 | (2-methylphenyl)-[4-(2,4-difluorophenyl)oxazol-2-yl]urea |
| 19 | (2-bromophenyl)-[4-(2,4-dichlorophenyl)oxazol-2-yl]urea |
| 20 | (2-ethylphenyl)-(4-methyloxazol-2-yl)urea |
| 21 | (2-methoxyphenyl)-(4-ethyloxazol-2-yl)urea |

-continued

| cmpd # | structure |
|---|---|
| 22 | (2,6-difluorophenyl)-[4-(2-naphthyl)oxazol-2-yl]urea |
| 23 | (2-methoxyphenyl)-[4-(methoxycarbonyl)oxazol-2-yl]urea |
| 24 | (2-methoxyphenyl)-[4-(carboxymethyl)oxazol-2-yl]urea. |

15. The compound according to claim 1, wherein said compound is any one of compounds 25 to 36;

| cmpd # | structure |
|---|---|
| 25 | (2,6-dichlorophenyl)-[4-(4-fluorophenyl)imidazol-2-yl]urea |
| 26 | (2,6-difluorophenyl)-(4-phenylimidazol-2-yl)urea |
| 27 | (2,6-dimethylphenyl)-[4-(2-methylphenyl)imidazol-2-yl]urea |
| 28 | (2,6-dibromophenyl)-[4-(4-fluoro-2-methylphenyl)imidazol-2-yl]urea |

-continued

| cmpd # | structure |
|---|---|
| 29 | 2-chlorophenyl-N-(4-methylimidazol-2-yl)urea |
| 30 | 2-methylphenyl-N-[4-(2,4-difluorophenyl)imidazol-2-yl]urea |
| 31 | 2-bromophenyl-N-[4-(2,4-dichlorophenyl)imidazol-2-yl]urea |
| 32 | 2-ethylphenyl-N-(4-methylimidazol-2-yl)urea |
| 33 | 2-methoxyphenyl-N-(4-ethylimidazol-2-yl)urea |
| 34 | 2,6-difluorophenyl-N-(4-(naphth-2-yl)imidazol-2-yl)urea |
| 35 | 2-methoxyphenyl-N-[4-(methoxycarbonyl)imidazol-2-yl]urea |

-continued

| cmpd # | structure |
|---|---|
| 36 | 2-methoxyphenyl-N-[4-(carboxymethyl)imidazol-2-yl]urea |

16. The compound according to claim 1, wherein said compound is:

[2,6-dichlorophenyl-N-[4-(4-fluorophenyl)thiazol-2-yl]urea]

17. A pharmaceutical composition comprising a compound according to claim 1 and a pharmaceutically acceptable carrier.

18. A method of treating inflammatory diseases, autoimmune diseases, destructive bone disorders, proliferative disorders, proliferative disorders, infectious diseases, neurodegenerative diseases, allergies, reperfusion/ischemia in stroke, heart attacks, angiogenic disorders, organ hypoxia, vascular hypersia, cardiac hypertrophy, thrombin-induced platelet aggregation or conditions associated with prostaglandin endoperoxidase synthase-2 in a patient, said method comprising administering to said patient a composition according to claim 17 in an amount effective to inhibit p38.

19. The method according to claim 18, wherein said method is used to treat an inflammatory disease selected from the group consisting of acute pancreatitis, chronic pancreatitis, asthma, allergies, and adult respiratory distress syndrome.

20. The method according to claim 18, wherein said method is used to treat an autoimmune disease selected from the group consisting of glomerulonephritis, rheumatoid, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, and graft vs. host disease.

21. The method according to claim 18, wherein said method is used to treat a desructive bone disorder selected from the group consisting of osteoarthritis, osteoporosis and multiple myeloma-related bone disorder.

22. The method according to claim 18, wherein said method is used to treat a proliferative disease selected from the group consisting of acute myelogenous leukemia, chronic myelogenous leukemia, metastatic melanoma, Kaposi's sarcoma, and multiple myeloma.

23. The method according to claim 18, wherein said method is used to treat an infectious disease selected from the group consisting of sepsis, sseptic shock, and Shigellosis.

24. The method according to claim 18, wherein said method is used to treat viral disease selected from the group consisting of acute hepatitis infection, HIV infection and CMV retinitis.

25. The method according to claim 18, wherein said method is used to treat a neurodegenerative disease selected from the group consisting of Alzheimers's disease, Parkinson's disease, cerebral ischemia and neurodegenerative disease caused by tramatic injury.

26. The method according to claim 18, wherein said method is used to treat ischemia/reperfusion in stroke or myocardial ischemia, renal ischemia, heart attacks, organ hypoxia or thrombin-induced platelet aggregation.

27. The method according to claim 18, wherein said method is used to treat a condition associated with prostaglandin endoperoxide synthase-2, wherein said condition is edema, fever, analgesia or pain.

28. The method according to claim 27, wherein said pain is selected from neuromuscular pain, headache, cancer pain, dental pain or arthritis pain.

29. The method according to claim 18, wherein said method is used to treat an angiogenic disorder selected from the group consisting of solid tumors, ocular neovasculization, and infantile haemangiomas.

30. A method of treating a p38-medicated condition in a patient in need thereof, said method comprising administering to said patient an effective amount of the composition according to claim 17.

31. A method of inhibiting p38, said method comprising contacting p38 with an effective amount of the compound according to claim 1.

32. A method of inhibiting p38, said method comprising contacting p38 with an effective amount of the composition according to claim 17.

* * * * *

UNITED STATES PATENT AND TRADEMARK OFFICE
CERTIFICATE OF CORRECTION

PATENT NO.     : 6,509,363 B2
DATED          : January 21, 2003
INVENTOR(S)    : Francesco Salituro, Guy Bemis and John Cochran It is certified that error appears in the above-identified patent and that said Letters Patent is hereby corrected as shown below:

<u>Title page,</u>
Item [60], change the Related U.S. Application Data, "Provisional application No." from "60/100,970" to -- 60/100,972 --.

Signed and Sealed this

Fifteenth Day of July, 2003

JAMES E. ROGAN
*Director of the United States Patent and Trademark Office*